United States Patent [19]

Krueger et al.

[11] Patent Number: 5,735,842
[45] Date of Patent: Apr. 7, 1998

[54] LOW PROFILE MANIPULATORS FOR HEART VALVE PROSTHESES

[75] Inventors: Kurt D. Krueger, Stacy; Michael J. Girard, Lino Lakes; Guy P. Vanney, Blaine, all of Minn.

[73] Assignee: St. Jude Medical, Inc., St. Paul, Minn.

[21] Appl. No.: 526,530

[22] Filed: Sep. 11, 1995

[51] Int. Cl.$^6$ .................................................. A61B 17/00
[52] U.S. Cl. ........................................................ 606/1; 623/2
[58] Field of Search ................................. 606/1; 623/2, 900

[56] References Cited

U.S. PATENT DOCUMENTS

| | | | |
|---|---|---|---|
| 3,546,710 | 12/1970 | Shumakov et al. | 3/1 |
| 3,574,865 | 4/1971 | Hamaker | 3/1 |
| 3,828,787 | 8/1974 | Anderson et al. | 128/303 |
| 3,860,005 | 1/1975 | Anderson et al. | 128/303 |
| 4,655,218 | 4/1987 | Kulik et al. | 128/321 |
| 4,683,883 | 8/1987 | Martin | 128/303 |
| 4,755,181 | 7/1988 | Igoe | 623/2 |
| 4,865,600 | 9/1989 | Carpentier et al. | 623/2 |
| 4,932,965 | 6/1990 | Phillips | 623/2 |
| 5,071,431 | 12/1991 | Sauter et al. | 623/2 |
| 5,163,954 | 11/1992 | Curcio et al. | 623/2 |
| 5,236,450 | 8/1993 | Scott | 623/2 |
| 5,289,817 | 3/1994 | Williams et al. | 600/204 |
| 5,339,802 | 8/1994 | Cook | 600/204 |
| 5,370,685 | 12/1994 | Stevens | 623/2 |
| 5,403,305 | 4/1995 | Sauter et al. | 606/1 |
| 5,425,705 | 6/1995 | Evard et al. | 604/28 |
| 5,433,700 | 7/1995 | Peters | 604/4 |
| 5,443,502 | 8/1995 | Caudillo et al. | 606/1 |

FOREIGN PATENT DOCUMENTS

| | | | |
|---|---|---|---|
| 043832 | 7/1991 | Germany . | |
| 990220 | 1/1983 | U.S.S.R. | 600/204 |
| 1690738 A1 | 11/1991 | U.S.S.R. . | |
| WO 94/18881 | 9/1994 | WIPO . | |
| WO 95/15715 | 6/1995 | WIPO . | |
| WO 95/17139 | 6/1995 | WIPO . | |

Primary Examiner—Michael H. Thaler
Attorney, Agent, or Firm—Hallie A. Finucane, Esq.

[57] ABSTRACT

A manipulable low profile heart valve holder that can be pivotally attached to a handle that permits the heart valve holder and a retained heart valve prosthesis to be manipulated remotely during implantation. The heart valve holder is pivotable from a position wherein the plane of the orifice of a retained heart valve is parallel to the axis of the handle, to a second position wherein the plane of the retained heart valve is substantially 90° to the axis of the handle. This pivoting arrangement particularly aids in manipulation of the heart valve prosthesis during implantation using trocars for access to the body cavity. Manipulation is accomplished by having controllable elements on the handle and retained on the exterior of the patient. Manipulation of the heart valve holder also may be done through separate instruments operating through separate trocars.

22 Claims, 24 Drawing Sheets

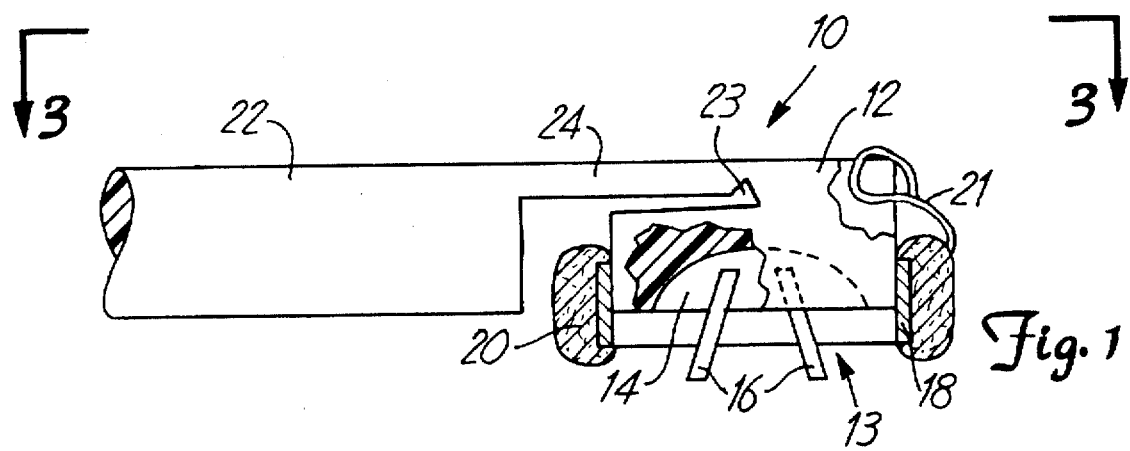
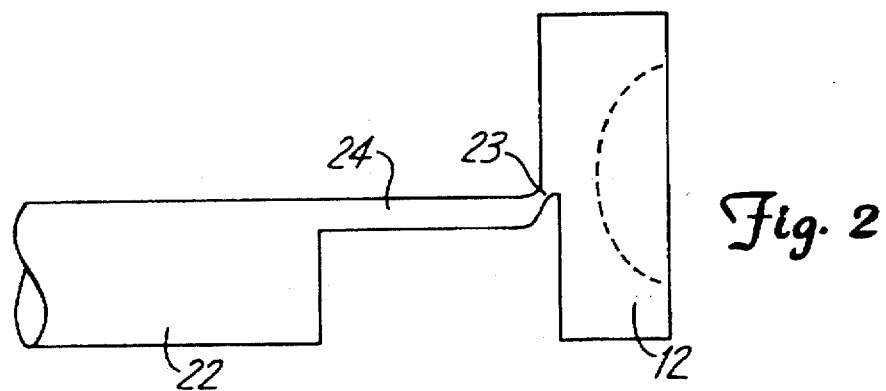
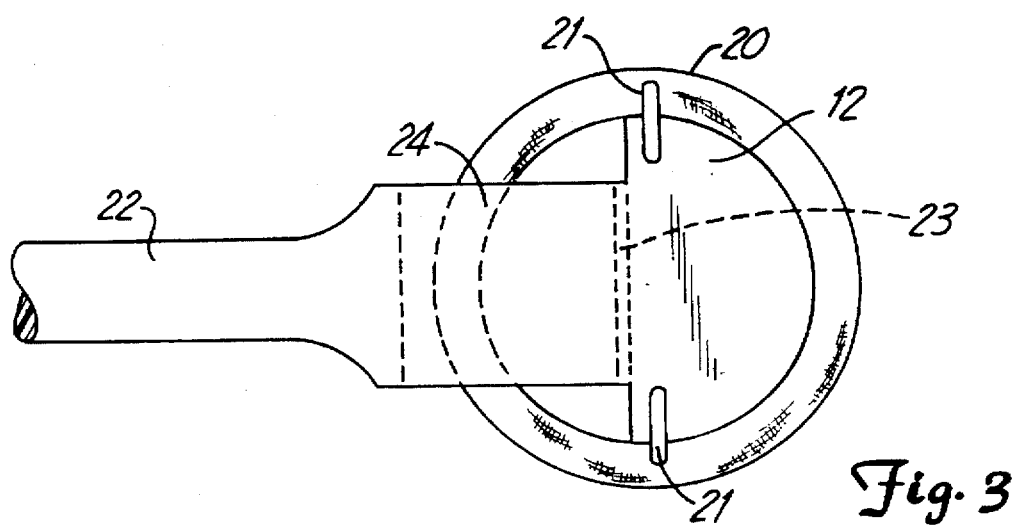

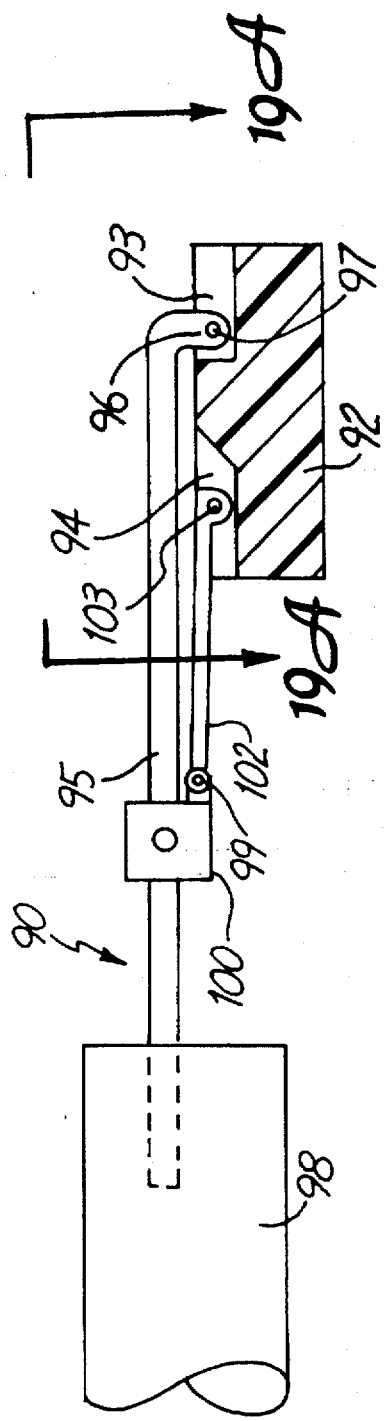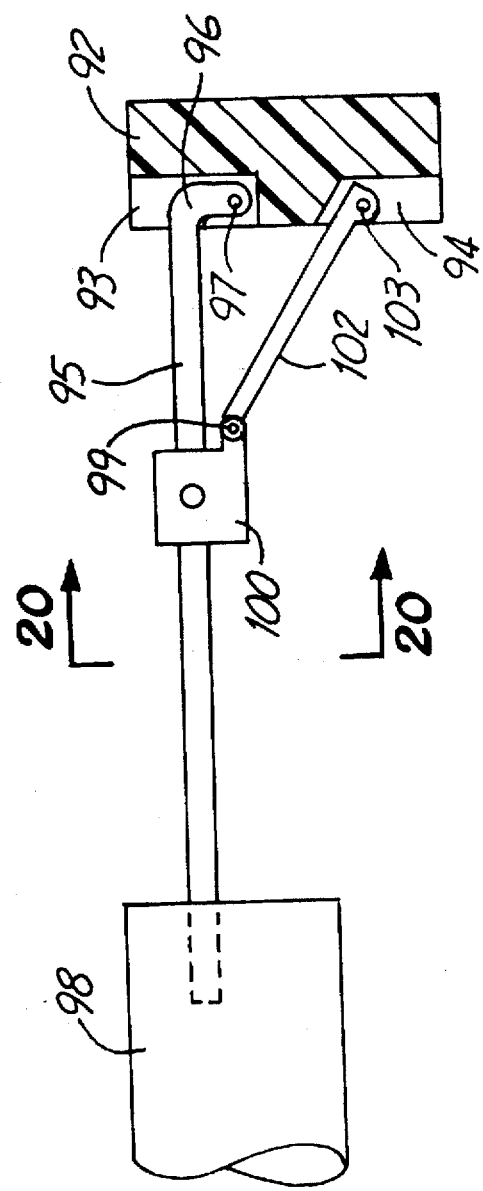

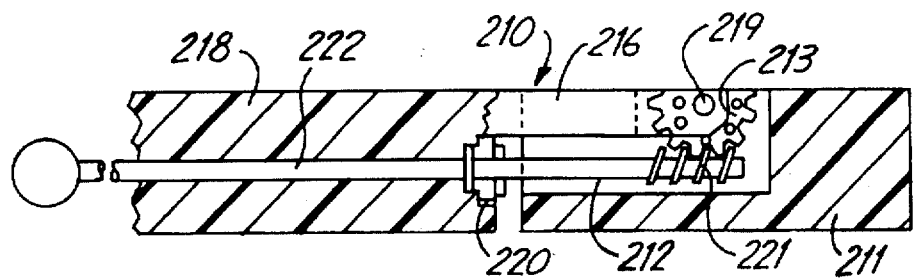
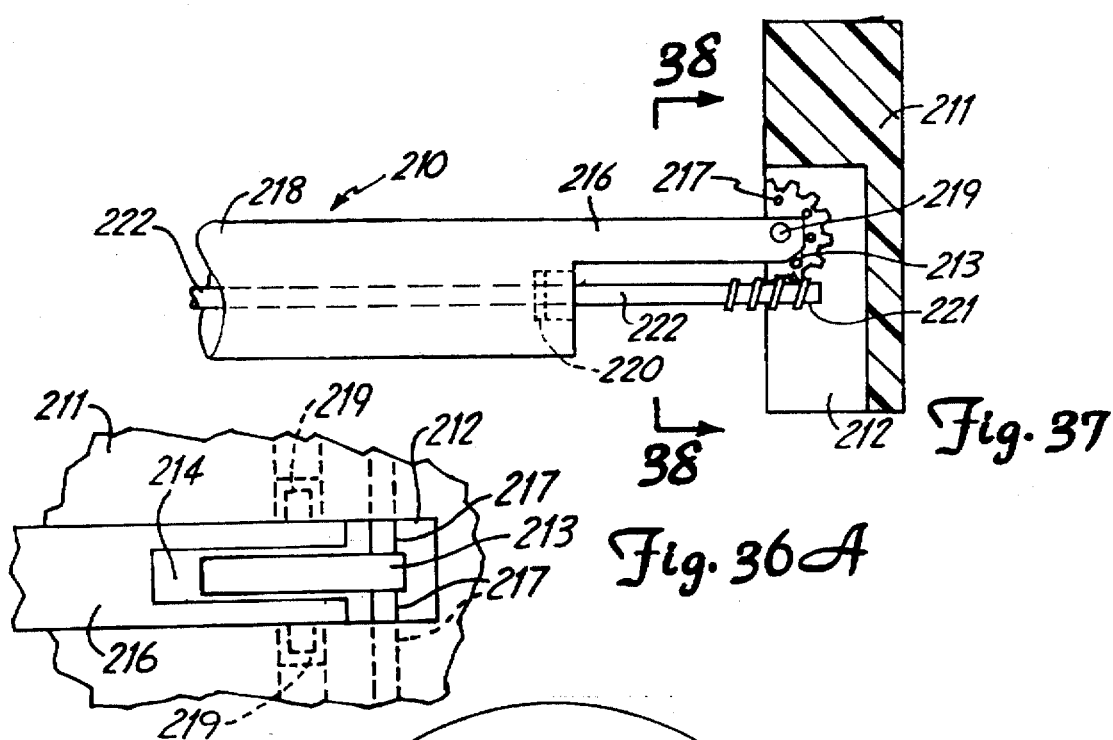
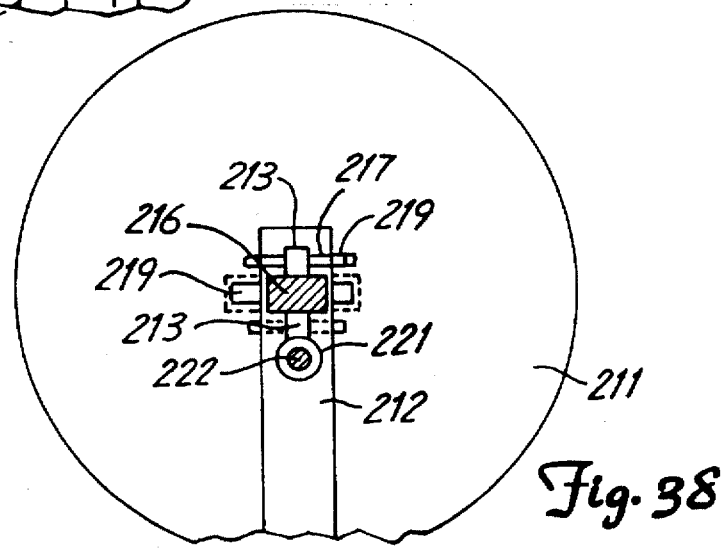

LOW PROFILE MANIPULATORS FOR HEART VALVE PROSTHESES

CROSS REFERENCE TO RELATED APPLICATION

Reference is made to United States patent application Ser. No. 08/449,145, filed May 24, 1995, now U.S. Pat. No. 5,578,076 entitled LOW PROFILE HOLDER FOR HEART VALVE PROSTHESIS.

FIELD OF THE INVENTION

The present invention relates to low profile heart valve holders that include attachments which permit changing the orientation of the holder and supported heart valve during implantation from a remote location.

BACKGROUND OF THE INVENTION

Holders for holding heart valve prostheses during implantation are known, and are used for positioning, holding, supporting and presenting the valve during surgery. Recently, a procedure has been developed where open heart surgery is performed through trocars, which are small tubular members placed in small incisions between ribs of the patient. This is described in International Publication No. WO94/18881, entitled METHOD FOR PERFORMING THOROSCOPIC CARDIAC BYPASS PROCEDURES. The procedure disclosed in the international publication uses elongated tools to operate on the heart and vessels through the trocars. This procedure can be used during heart valve prosthesis implantation. The advantage of the trocar procedure is that the trauma to the chest associated with traditional open heart surgery is substantially reduced, the subsequent recovery period is also reduced. When a heart valve prosthesis is inserted through a trocar, extreme care has to be taken to protect the occluders in the valve, and once inserted, it becomes desirable to change the orientation of the valve prior to implanting to simplify the suturing of the heart valve prosthesis in place.

Also, International Publication No. WO 95/15715 entitled DEVICES AND METHODS FOR INTRACARDIAC PROCEDURES discloses a type of actuator for moving a heart valve holder between two positions and explains various procedures in detail.

SUMMARY OF THE INVENTION

A low profile device for holding a heart valve prosthesis includes a handle coupled to a holder so that the holder and attached valve can be pivoted substantially 90° from an initial insertion position wherein the handle is parallel to the plane of the heart valve orifice ring. This permits the handle, holder, and supported heart valve prosthesis to be inserted through a trocar and subsequently the holder can be manipulated by pivoting it relative to the handle to position it in a most advantageous location and orientation for suturing, the valve. The valve prosthesis to the tissue annulus that remaining after the surgical excision of the parent's native heart valve, referred to herein as "tissue annulus".

The present invention relates to the connections of the handles to the heart valve holders. Specifically, the invention relates to the method used to pivot the valve from a position where the plane of the valve orifice is parallel with the handle to a position where it is perpendicular to the handle. The holders can be of any desired type that will fit the needs of a low profile presentation of the heart valve orifice ring to the thoroscopic surgical environment. The holder can be formed to protect the occluder or occluders during implantation, and the subsequent removal of the holder.

Both mitral and aortic heart valve holder mechanisms for attachment to the handle of the holder can be utilized, using the handle connectors and handles of the present invention.

Embodiments of the present invention include linkages and connections for positively moving the heart valve holder about its pivoting connections to the desired configuration from a remote location, outside the patient's body. Other embodiments can be pivoted to position by manipulating with instruments through separate trocars used for the suturing and implantation process.

BRIEF DESCRIPTION OF THE DRAWINGS

FIG. 1 is a side elevational view of a handle and a manipulatable heart valve holder supporting a heart valve prosthesis made according to the present invention;

FIG. 2 is a side elevational view of FIG. 1 showing the heart valve holder pivoted 90° from its position in FIG. 1 with the heart valve prosthesis removed;

FIG. 3 is a plan view taken generally along line 3—3 in FIG. 1;

FIG. 18 is a side elevational view of a further modified form of the present invention using a slider linkage for pivoting the heart valve holder;

FIG. 19 is a side elevational view of the device of FIG. 18 shown in a second position;

FIG. 36 is a further modified form of the invention illustrating the use of a gear drive arrangement for pivoting a heart valve holder;

FIG. 36A is an enlarged top view of the attachment point and gear drive for the unit shown in FIG. 36;

FIG. 37 is a side elevational view of the device of FIG. 36 with the valve holder in a modified position;

FIG. 38 is a view taken as on line 38—38 in FIG. 40;

DETAILED DESCRIPTION OF THE PREFERRED EMBODIMENTS

Figure 4:
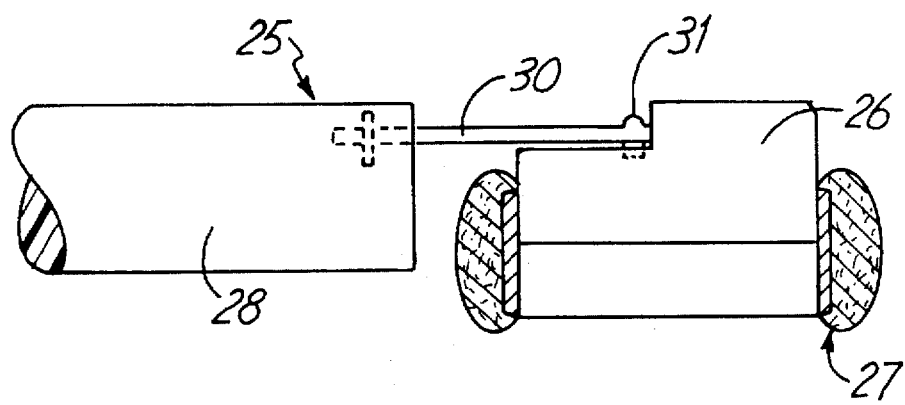
FIG. 4 is a side elevational view of a heart valve holder and handle made according to a modified form of the invention.

It is desired to have a prosthetic valve holder and handle which will allow a surgeon to adjust the position of the heart valve supported on the holder with respect to the handle. The orientation of the plane of the valve orifice is parallel to the axis of the handle, in one position and perpendicular to the axis of the handle in a second position. With suitable attachment points, the valve holder can pivot more than 90° from its retracted or compact position for insertion to its activated, operating position for implantation.

In its simplest form, the heart valve holder, and supported heart valve prosthesis, is capable of being pivoted manually relative to a handle, so that the holder can be manipulated as desired for implantation. Implantations presently are being carried out by the use of trocars or similar devices, such as cannulas. Trocars are small tubular members inserted between the ribs with very little spreading of the ribs, having a limited opening so that there is no excessive trauma to the chest. More than one trocar can be used. Pivoting the holder and retained heart valve prosthesis relative to the handle permits moving the heart valve prosthesis in an appropriate position within the chest cavity. The valve holder and heart valve prosthesis can be pivoted to a desired orientation with external manipulation such as a separate tool inserted through a separate trocar or a remote external control linked to the heart valve holder.

In FIGS. 1–12, typical possible forms of the invention that permit pivoting of a heart valve holder relative to a handle connecting member and handle are shown. In FIG. 1, a low profile handle and heart valve holder 10 includes a heart valve holder 12 and a handle 22. Valve holder 12 is of a sufficient size to hold a valve prosthesis 13 by being inserted into the orifice of the heart valve prosthesis. The valve holder 12 can have a suitable recess shown at 14 to accommodate occluders 16 of the heart valve prosthesis. Heart valve prostheses normally will have an orifice ring member 18, with a suture ring 20 around the periphery. Heart valve 13 must also be affixed to holder 12. FIG. 1 shows suture 21 passing through openings in the holder and through the sewing ring. Friction holding between the valve orifice ring 18 and the outer periphery of the heart valve holder 12 also is possible, as desired.

The heart valve holder 12 in the present invention as shown in FIG. 1 can be molded or formed in other procedures from a suitable polymeric material, such as a plastic that is capable of being maintained in a sterile condition for operating. As shown in FIGS. 1 and 2 the heart valve holder 12 is integrally molded to a handle 22, that is of any desired length so that the holder and heart valve can be manipulated by a surgeon from a remote location outside of the patient. The connection to the heart valve holder can be a handle mounting member which can be coupled to additional handle sections. Handle 22 is joined to the holder 12 through a support structure 24. Valve holder 12 is hingedly connected to support structure 24 at a hinge connector formed by making a notch 23 at a distal end of support structure 24.

This type of plastic hinging is well known and is used in various molding techniques, and provides a way of permitting the heart valve holder 12 and the supported heart valve prosthesis 13 to be manipulated to position for insertion through a trocar and then pivoted into a selected position to facilitate the seating of the valve into the tissue annulus. The heart valve holder 12 can then be removed. The heart valve holder is pivoted relative to the handle 22 at the hinge connector 23.

It should be noted that the only junction between the handle 22, connector 23 and the heart valve holder 12 is through the support structure 24 so that the heart valve holder 12 is free to pivot and can be manipulated by external forces such as surgical instruments that are inserted through separate trocars in a patent for positioning the heart valve prosthesis 13 in a desired location for suturing into place prior to removal of the heart valve holder 12 from the implanted prosthesis 13.

FIG. 3 is a schematic top view of the device of FIG. 1, schematically showing the integral molding of hinge connector 23 along support structure 24. The molding can be accomplished merely by placing suitable blocks or forms to provide a slit separating the hinge connector 23 from the underlying portion of the heart valve holder 12. The hinge connector 23 and support structure 24 may be made by separate pieces fastened together, as well as by molding.

Figure 5:
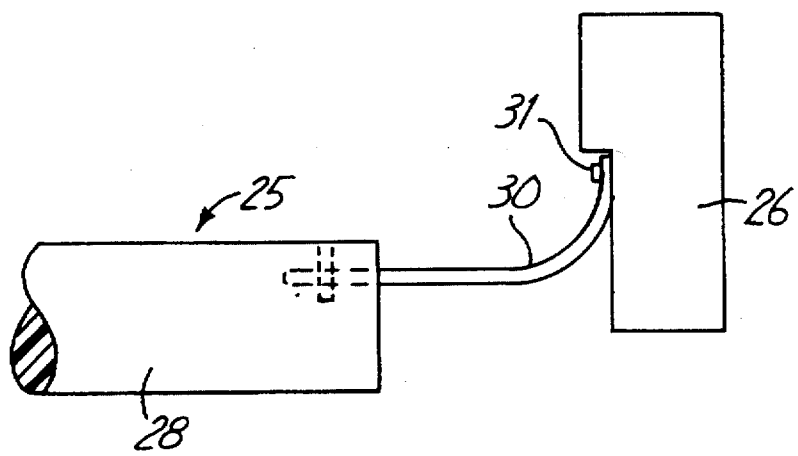
FIG. 5 is a side elevational view of the device of FIG. 4 shown with the heart valve holder pivoted 90° and with the heart valve prosthesis removed.

FIGS. 4 and 5 show a modification of the device of FIG. 1. In this second form of the invention, an assembly 25 of a handle 28 and heart valve holder 26 is shown. Heart valve holder 26 is formed to hold or support a heart valve prosthesis shown at 27, and the holder 26 can be sutured in place to the heart valve prosthesis 27 as previously mentioned. Handle 28 is used for manipulating the heart valve holder 26 and the attached heart valve prosthesis 27. The handle 28 is connected to the heart valve holder 26 with a hinge connector section 30 that is a separately formed flat strap, or cylindrical in cross section, and is secured as at 31 to the heart valve holder 26 in a suitable manner. The securement can be through known fasteners, suitable adhesives or molded directly into the assembly. The hinge connector 30 may be a flat strap is similar to that shown at 23 in FIG. 1. The hinge connector 30 may be molded as part of handle 28 or also inserted in and fastened in with a pin or screw in the handle 28 itself. The two holder positions 90° apart are shown by way of reference in FIGS. 4 and 5 to indicate that the connector 30 can be hingedly connected to the heart valve holder 26. The material that is used may be a malleable polymeric or metallic material that will hinge as shown, or can be a "shape memory" type material such as Tinel®, a well known nickel-titanium shape memory alloy made by Raychem Corporation, so that once bent into the shape shown in FIG. 5 it will remain in that position until a further bending force is applied to the heart valve holder 26 relative to the handle 28.

The hinge connector 30, as well as the connector 23 in FIG. 1 have to be made with sufficient rigidity such that the assembly remains in the desired position throughout the procedure. Normal procedures performed by the surgeon should not cause hinged connector 30 to bend or distort from the desired position during use. The heart valve holder 26 and its supported heart valve prosthesis 27 should not cause unwanted bending or movement during use. The hinge connector 30 is bendable and has to have sufficient yielding so that holder 26 and valve 27 can be bent to its desired position.

The heart valve holders shown in FIGS. 1–5 may be placed in the position shown in FIGS. 1 and 4 for insertion through a trocar, and then moved to an activated position as shown in FIGS. 2 and 5 for implantation of the heart valve and suturing the valve in place. The heart valve holder and heart valve can be oriented anywhere between these two positions.

Since the suture ring 20 of a heart valve prosthesis 27 is generally circular, the trocar opening has to be large enough to accommodate the valve and holder with the plane of the valve parallel to the handle axis (FIG. 4). Preferably the periphery of handle 28 does not protrude beyond the periphery defined by the surfaces of the heart valve and heart valve holder, in other words, the handle and valve holder are coplanar. Preferably, the cross section of the handle should not increase the profile of the valve holder assembly. It is desirable to lock the holder and prosthesis in the two positions of the holder.

Figure 6:
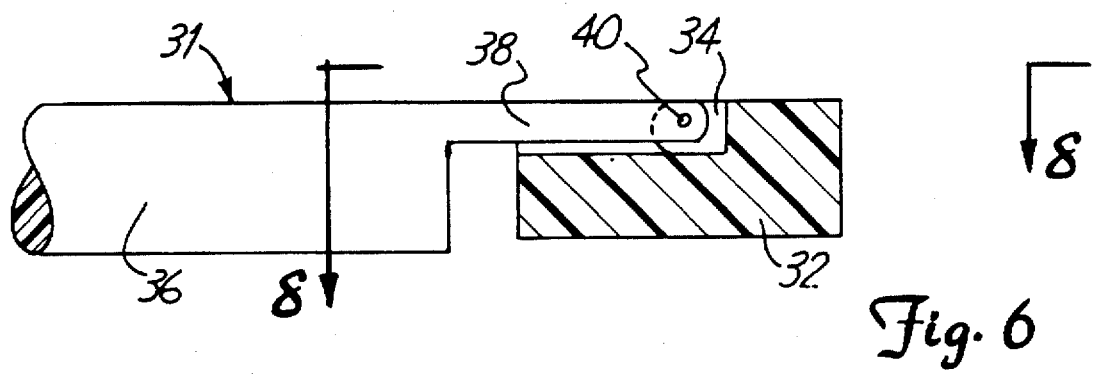
FIG. 6 is a side elevational view of another heart valve holder and handle using a pivoting pin for connecting the handle to the heart valve holder.
Figure 7:
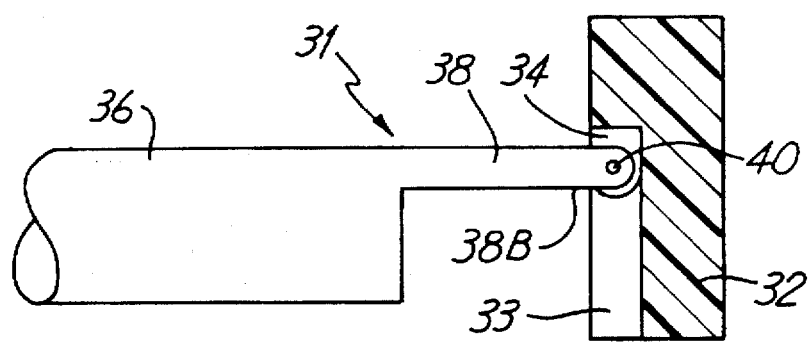
FIG. 7 is a side elevational view of the device of FIG. 6 in a pivoted position.
Figure 8:
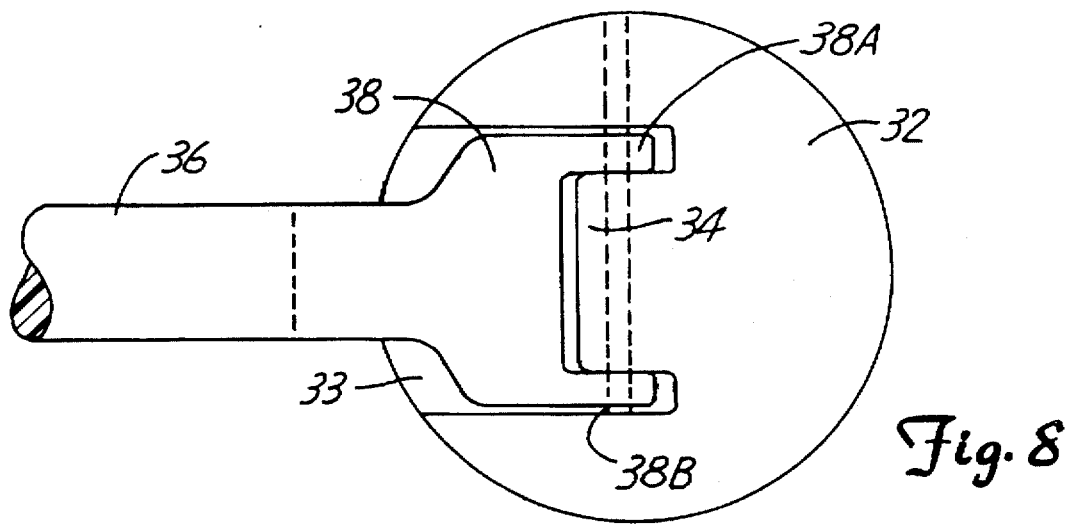
FIG. 8 is a plan view of the device of FIG. 7 taken along line 8—8 in FIG. 6.

A pin type hinge may be utilized for pivoting the heart valve holders relative to handles as well. FIG. 6, 7 and 8 show one form of this type of a holder. A heart valve holder and handle connector or handle assembly 31 includes a heart valve holder 32 that is made as previously explained, and which will support a heart valve prosthesis.

In FIG. 5, and in FIGS. 6, 7 and 8, as well as in all of the following figures, no heart valve prosthesis is illustrated on the respective heart valve holders for sake of clarity. However, each heart valve holder shown would carry a heart valve prosthesis exemplified by heart valves 13 and 27.

The heart valve holder 32 of FIGS. 6, 7 and 8 is formed to have a recess 33 extending from the center portions to one edge. The recess 33 forms a hinge pin carrier 34 that has spaces along opposite sides thereof. In this form of the invention, a heart valve holder handle 36 is provided with a connector portion 38 that is bifurcated, that is, it has two side flanges 38A and 38B (see FIG. 8), that fit on opposite sides of the hinge pin carrier 34. A suitable hinge pin 40 can then be passed through the flanges 38A and 38B as well as through a provided opening in the carrier 34 to provide a hinge pin. The hinge pin 40 can be made of any suitable material such as stainless steel, or other metals that are suitable for use in the implantation of prostheses. Polymeric pins can also be utilized. Normally the heart valve holder is made of a suitable polymeric material, such as a plastic and the handle is also of a polymeric material that can be molded to form the bifurcated connector 38. The cross section of the connector 38 can be either circular or rectangular as desired, and should have the desired amount of stiffness so that it will support the holder 32 and the heart valve prosthesis supported on the holder 32 during the implantation process. The carrier 34 and flanges 38 can be provided with detents to retain the holder in the holder's two positions.

FIGS. 9, 10, 11 and 12 illustrate a hinge made for limited universal pivoting movement by use of a ball and socket connection. In this embodiment of the invention, a heart valve holder 42 again is formed to retain a suitable heart valve prosthesis, and can be formed in any desired configuration. The heart valve holder 42 is provided with a recess 43 along one side thereof into the center of the holder, and a ball socket 44 is formed in the heart valve holder 42 and opens to the recess 43. The recess 43 also opens upwardly from the ball socket, so that the ball is held in place in the socket as shown perhaps best in FIG. 12 by having the socket 44 arranged appropriately for retaining the generally spherical ball 45 in the socket 44. When the heart valve holder 42 is made of a polymeric material, the ball 45 can be snapped into place in the socket. If needed, a ball retainer washer or ring can be used to retain ball 45 in socket 44. As shown, the ball 45 forms a hinge that is molded to or fixed to a connector 46, which is attached in turn to a handle 48 of the assembly 49 of the handle 48 and holder 42.

Figure 10:
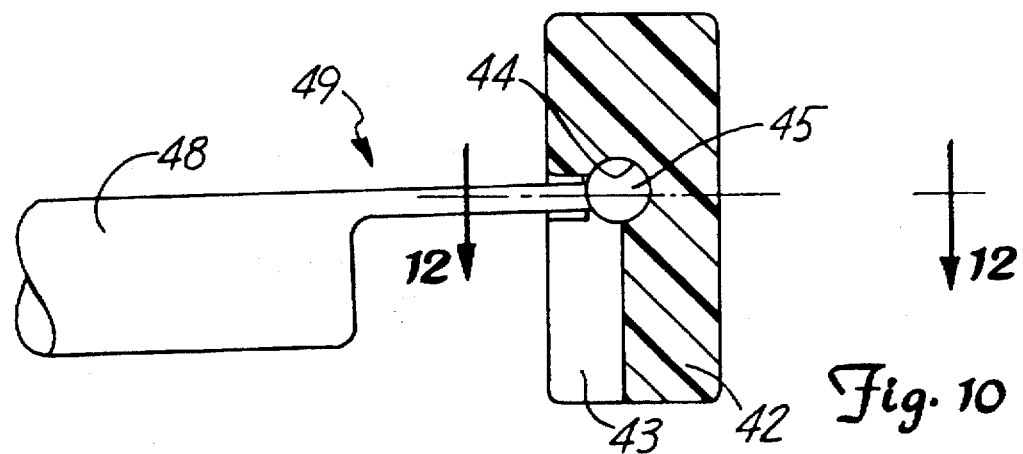
FIG. 10 is a view of the device of FIG. 9 with the heart valve holder pivoted 90°.
Figure 11:
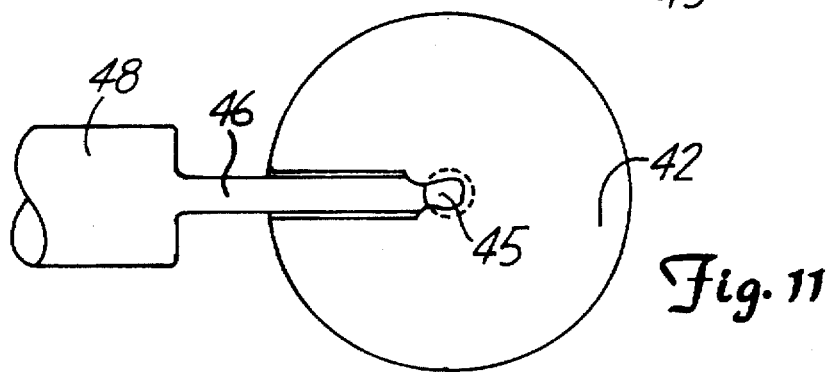
FIG. 11 is a fragmentary top plan view of the device of FIG. 9 taken on line 11—11 in FIG. 9.

As can be seen in FIG. 10, the ball 45 will pivot in the socket 44 so that the heart valve holder 42 can pivot a full 90°, and perhaps slightly more if the ball socket 44 and ball 45 are configured appropriately. A suitable detent can be used to retain the holder 42 in this position.

Figure 9:
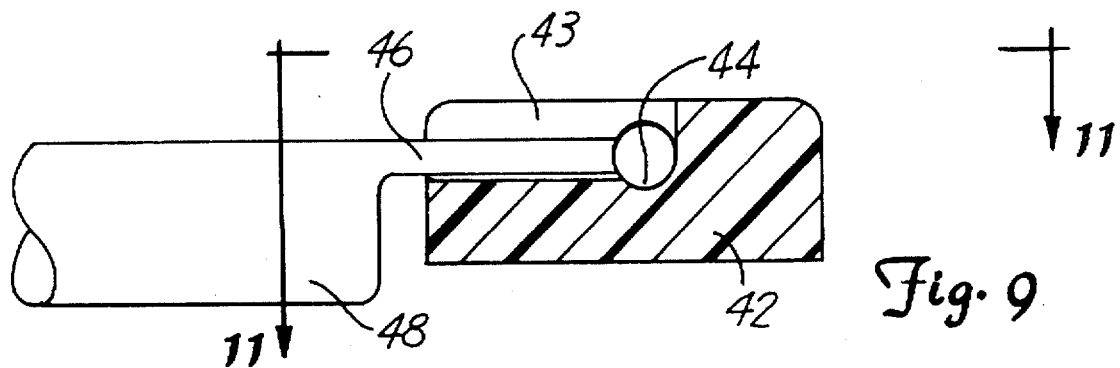
FIG. 9 is a sectional view of a further modified form of the invention showing a ball and socket joint for connecting a heart valve holder to a handle.
Figure 12:
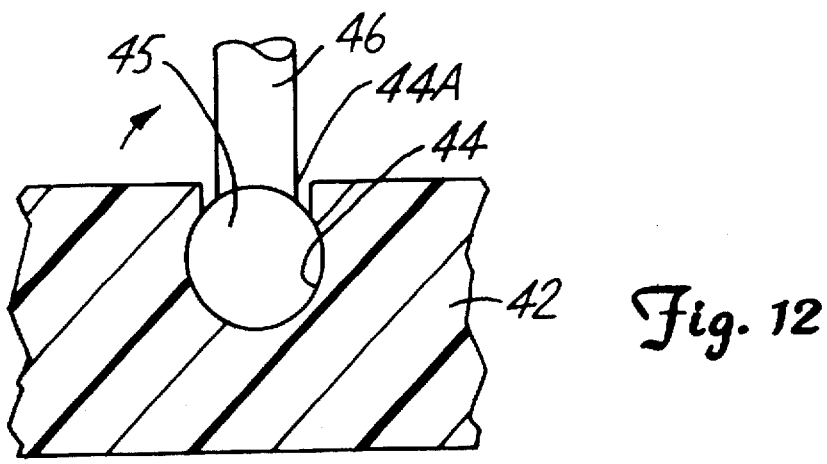
FIG. 12 is a sectional view taken along line 12—12 in FIG. 10 with the FIG. 12 located 90° from its orientation.

Further, as shown in FIG. 12, the ball socket gap shown at 44A along the sides of the socket opening to the recess 43 provides sufficient clearance for the connector 46 so that there can be a slight tilting of the heart valve holder 42 about an axis 90° to the primary hinge axis for pivoting the heart valve holder between the positions shown in FIGS. 9 and 10.

The handle 48 can be of any desired length so that the holder 42 and any heart valve prosthesis held thereby can be inserted through a trocar into a desired location for implantation. After implantation, the handle 48 can be used for permitting removal of the holder 42 from the heart valve prosthesis. In removing the holder 42 and handle 48 from the trocar, remote actuation from a proximal end of the handle may be provided.

Figure 13:
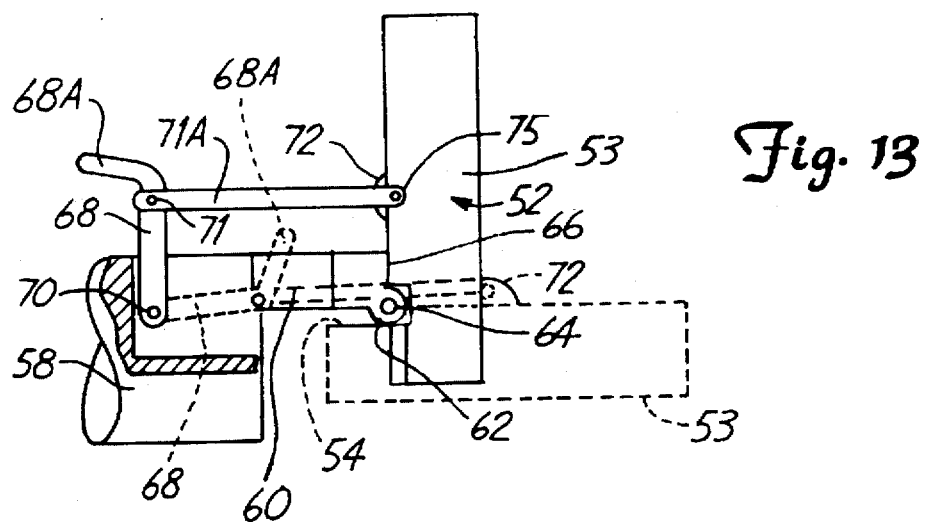
FIG. 13 is a schematic side elevational view of a handle and heart valve holder utilizing a 4-bar linkage actuator and connector.
Figure 14:
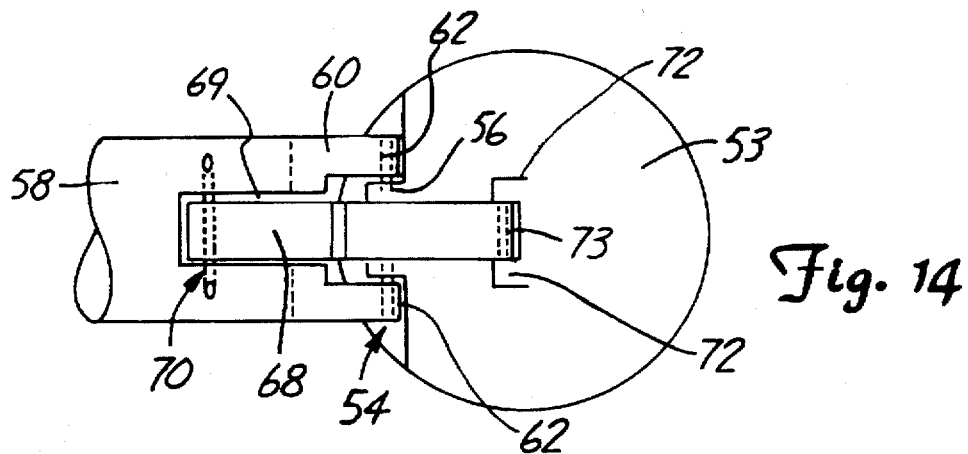
FIG. 14 is a top plan view of the device in FIG. 13 with the valve holder in a position 90° from FIG. 13.

FIGS. 13 and 14 illustrate a simplified schematic representation of an actuator that can be utilized for tilting the heart valve holder from an activated position to a retracted position. The connection shown utilizes a 4-bar linkage that is added to the valve holder and handle assembly, and can actually be added to the holders of FIGS. 1 and 2, as well as the holder of FIGS. 6, 7 and 8. In this form of the invention, however, a heart valve holder and handle assembly 52 which can be formed of suitable polymeric material includes a heart valve holder 53 which is provided with a recess 54 that forms a lug 56, similar to the hinge pin carrier 34 in FIG. 8. In this form of the invention, a handle 58 has a connector end 60 that is also bifurcated and has side fingers or flanges 62 that fit on opposite sides of the lug 56, and a suitable pin or pins illustrated at 64 can be passed through provided openings in the fingers or flanges 62 and the lug 56 to form a hinge pin for permitting the valve holder 52 to pivot between two positions 90° apart including the low profile position and a position 90° to the low profile position. In this form of the invention, the end of the flanges 62 should protrude beyond a stop surface 66 that is provided at the end of the flanges so that the pivot pin 64 can be utilized through the hub 56 and yet permit the valve holder 52 to be pivoted relative to the handle connector 60.

Further, in this form of the invention, a lever that is relatively of small size indicated at 68 is pivoted in a recess 69 formed near the distal end of the handle 58. This recess can be formed to the size desired, and as shown in FIG. 14, the recess 69 can have some width. An aperture is provided in the handle 58 into which a pivot pin 70 can be passed to pivot the lever in a desired location. This lever 68 has a thumb actuator end 68A that can be activated by the thumb of the surgeon for operation. The lever 68 in turn is pivotally mounted with a suitable pin 71 at a pivot axis connecting lever 68 to a link 71A. The link 71A in turn is connected to the heart valve holder 53 at a location spaced a desired distance from the pin 64. The distance is selected so that a line between the axes of pins 64 and 70 is parallel to the link 71A.

In this form of the invention, the heart valve holder 53 has integral ears 72, 72 formed therein in the center portions of the heart valve holder, to form a space into which a lug end portion 73 of the link 71A is received. A pin 75 passes through the ears 72, 72 and the end portion 73 of the link 71A.

In operation, from the solid line position shown in FIG. 13, the thumb lever 68 can be pushed forwardly to its dotted line position so that the valve holder moves to its dotted line position. In this form then the link 71A acts to cause the valve holder 53 to pivot on pin 64 between its two positions 90° from each other. The length of the link 71A and the distance between the pins 70 and 64 can be selected and changed to accommodate trocars of different lengths. The form shown is schematic only, and the size can be selected as needed. The length of connector 60 also can be selected to insure operability of the lever 68 on the exterior of the trocar. The form of the invention shown in FIGS. 13 and 14 provide for manipulation of the valve holder into its desired position during implantation from the handle proximal end, exterior of the patent's body.

Figure 15:
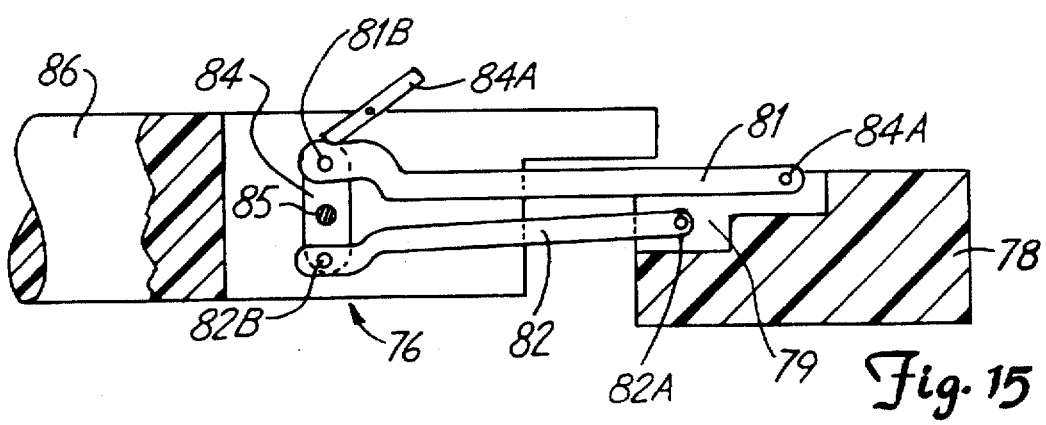
FIG. 15 is a schematic side elevational view of a modified 4-bar linkage connecting a heart valve holder to a handle.
Figure 16:
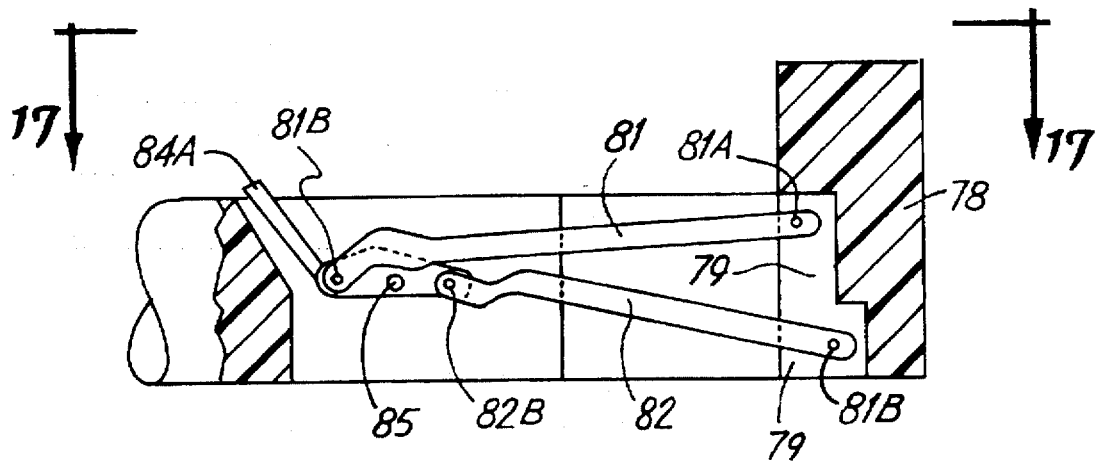
FIG. 16 is a side elevational view of the device of FIG. 15 with the valve holder pivoted 90 from that shown in FIG. 15.
Figure 17:
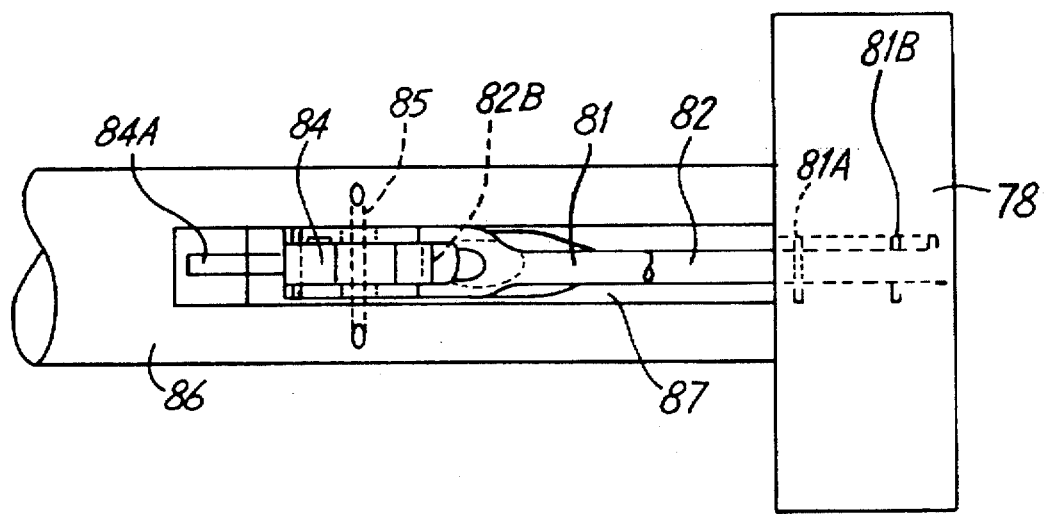
FIG. 17 is a plan view of the device shown in FIG. 16 taken on line 17—17 in FIG. 16.

FIGS. 15, 16 and 17 illustrate a modification of the 4-bar linkage shown in FIGS. 13 and 14. In this form of the invention, the heart valve holder and handle assembly indicated generally at 76 includes a heart valve holder 78 formed of suitable material such as a polymer, and a handle or handle connector 86. The heart valve holder has a recess 79 formed therein of suitable size to accept a pair of links 81 and 82, respectively. The links 81 and 82 form part of a 4-bar linkage assembly, and have ends pivotally connected with pins 81A and 82A to the heart valve holder 78. The opposite ends of the links 81 and 82 are connected with suitable pins 81B and 82B to an actuator link 84 of suitable length. The actuator link 84 is pivotally mounted with a suitable pin 85 to handle member 86. The handle member 86 is bifurcated, as shown in FIG. 17, with a slot 87 to receive the links 81 and 82 and the actuator link 84. The actuator link 84 has a tab 84A, for example, which can be manipulated manually. The actuator link 84 also can be operated with a separate tool, or an actuator, such as a push rod.

In this form of actuation, when the pivot point 81B is rotated to the left as shown in FIG. 15, pivot point 82B rotates to the right. The link 81 retracts, and the link 82 extends relative to the handle 86, and this causes the heart valve holder 78 to pivot on the ends of the links at pivots 81A and 82A so that it can be moved to the position shown in FIG. 16. FIG. 16 indicates that the heart valve holder 78 is at 90° to the position shown in FIG. 15.

The manipulation of the actuator link 84 can be accomplished by pulling or pushing on one of the links 81 or 82 with a suitable tool while in the interior of a chest cavity, if desired, or some other type of actuator can be utilized for externally operating the actuator link 84.

It should be noted that the parallel links in other forms of the invention just described form connectors for connecting the heart valve holder to the handle, and thus are handle connectors.

Figure 20:
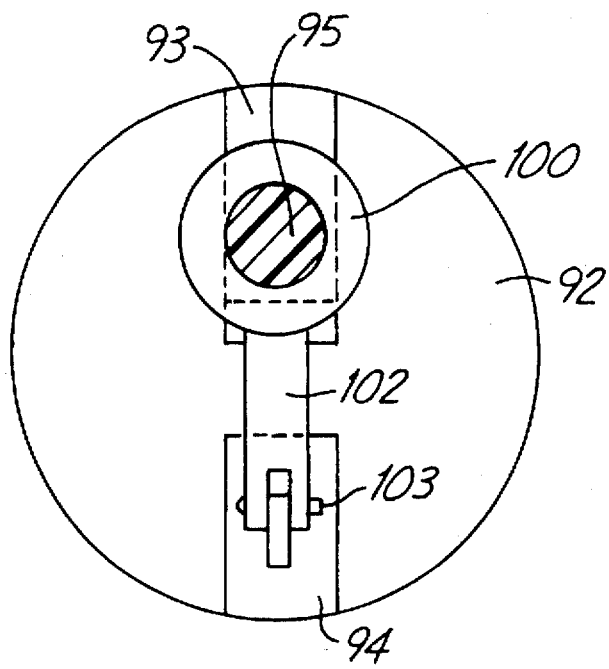
FIG. 20 is a fragmentary sectional view taken as on line 20—20 in FIG. 19.
Figure 19A:
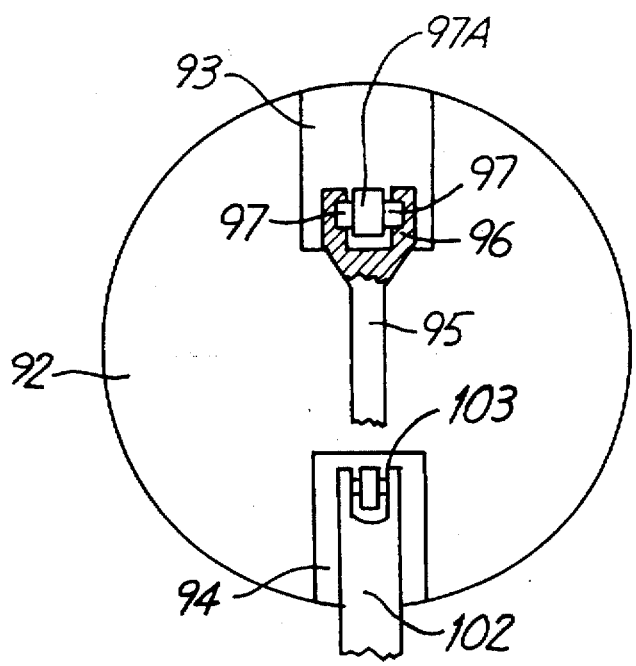
FIG. 19A is a plan view taken on line 19A—19A in FIG. 18.

The form of the invention shown in FIGS. 18, 19, and 20 includes a slider mechanism for actuating a heart valve holder between two positions. It involves pivoting connecting links as well. In this form of the invention, a handle and holder assembly 90 includes a heart valve holder 92 that is provided with a pair of recesses in the upper surface indicated at 93 and 94. A first connector link 95 has an end portion that is bent downwardly as shown at 96 and is joined pivotally with pins at 97 to the heart valve holder 92. The pins 97 are formed on a molded attachment post 97A (See FIG. 19A) The connector link 95 forms a connector to a handle member 98, and can be held on the handle member 98 in any desired manner. It can be, for example, inserted into a recess in the handle and secured in place, or it can be integrally molded in the handle 98.

A sleeve or slider 100 is slidably mounted on the link 95, and the slider in turn pivotally connects to an actuator link 102 at a pivot 99. The link 102 has an end portion pivotally mounted as at 103 to the heart valve holder 92 at a location spaced from the pivot pin 97.

When the slider 100 is slid along the connector link 95, the actuator link 102 will cause the heart valve holder 92 to pivot on pivot pins 97 to its position shown in FIG. 19.

The pins that are used can, again, be of any desired form of a pivot pin including biocompatible metals, such as stainless steel, or of polymeric materials.

Figure 21:
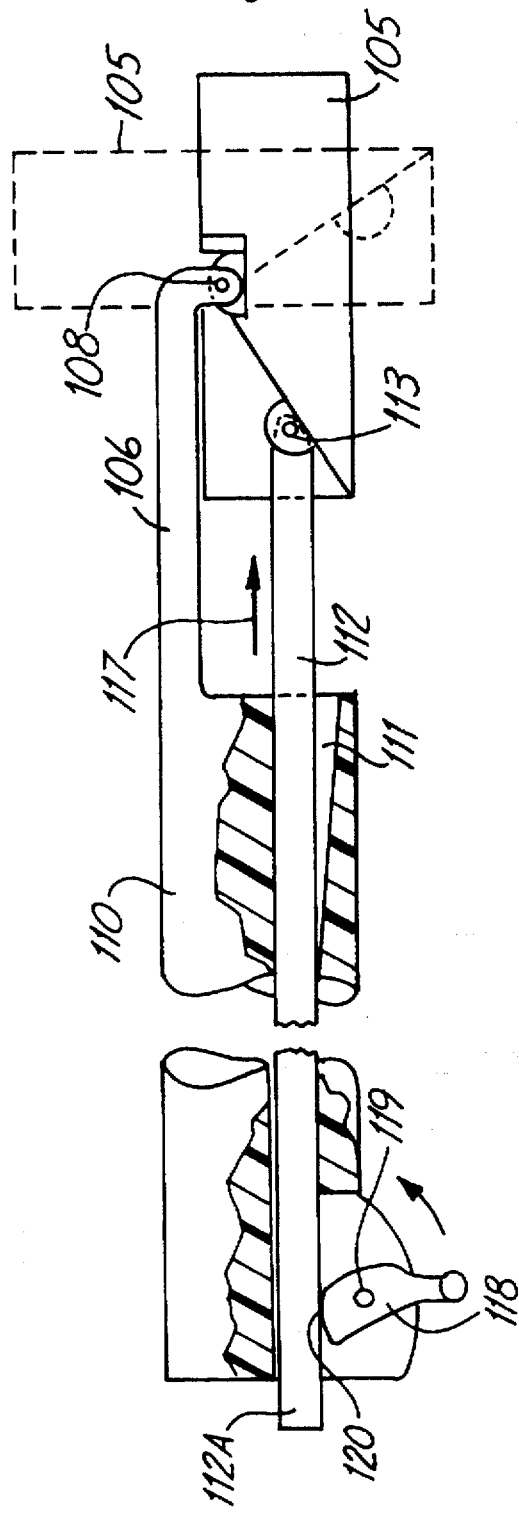
FIG. 21 is a side elevational view of a further modified slider mechanism utilizing a push rod that is remote from the valve holder for pivoting the valve holder and which incorporates a cam locking mechanism.
Figure 22:
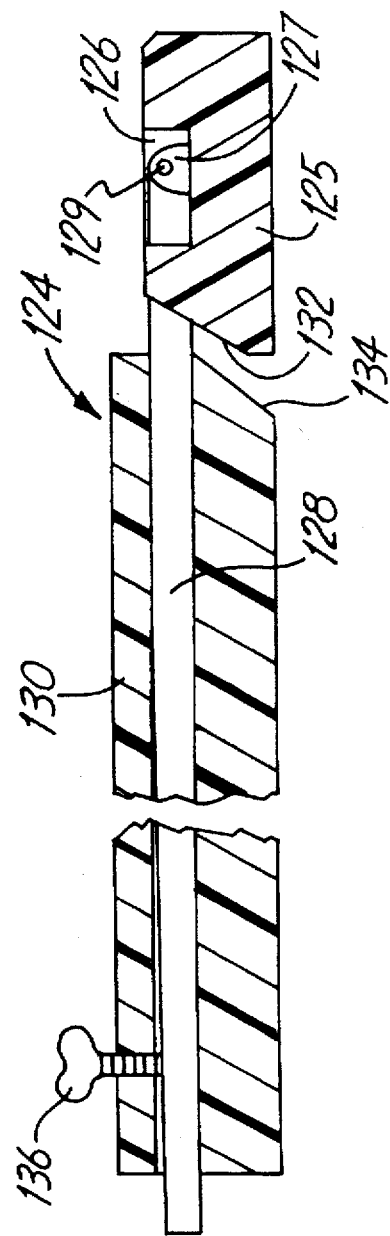
FIG. 22 is a schematic part sectional view of a further modified form of the present invention using a thumbscrew lock for an actuator.
Figure 23:
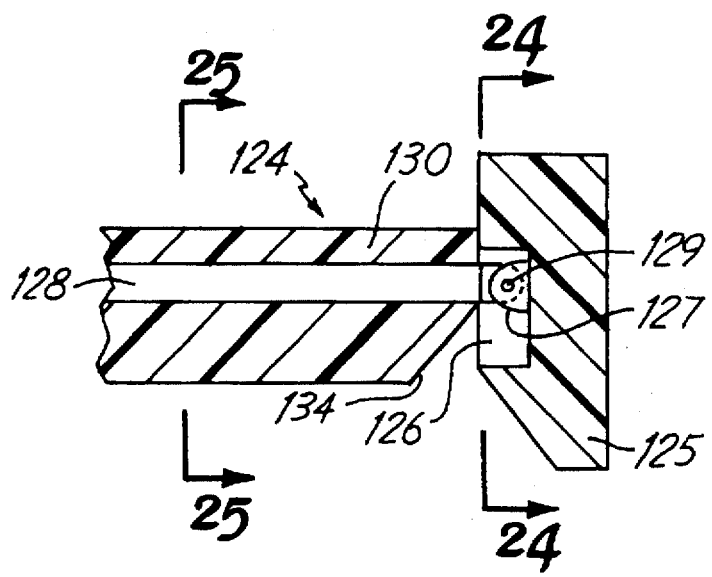
FIG. 23 is a side elevational view of the device of FIG. 22 shown pivoted 90° from its position in FIG. 22.
Figure 24:
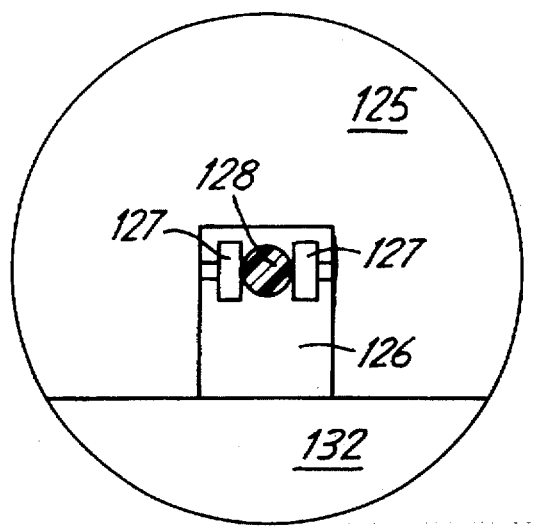
FIG. 24 is a sectional view taken as on line 24—24 in FIG. 23.
Figure 25:
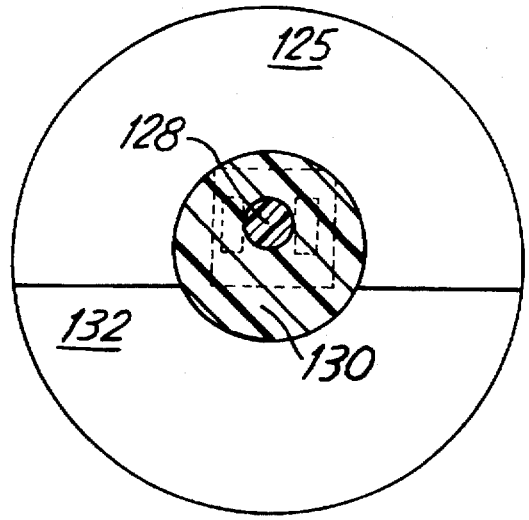
FIG. 25 is a sectional view taken as on line 25—25 in FIG. 22.

FIG. 21 is a modified form of a slider for an actuator, and includes a heart valve holder 105 that has a first connector link 106 pivotally mounted as at 108 in a recess of the upper side of the heart valve holder. A suitable pin is used for forming the pivot connection 108, while permitting the heart valve holder to pivot between desired positions. The connector link 106 is attached to a handle 110, and the handle is provided with a channel or passageway indicated at 111 for receiving a push rod 112. The push rod 112 extends parallel to the link 106, and is pivotally mounted as at 113 to suitable ears in a suitable recess on the heart valve holder 105. The proximal portion of the push rod is accessible from a proximal end of the handle 112A, and by pushing the rod 112 in direction as indicated by the arrow 117, the heart valve holder 105 can be moved or pivoted to its dotted line position by remote actuation. The end 112A is accessible to the surgeon that is performing the implant from a remote locate outside of the patient's body, so that the heart valve holder 105 and a heart valve prosthesis supported thereon can be manipulated to a desired location.

In this form of the invention, a cam lever 118 is pivotally mounted as at 119 to a provided portion of the handle aligned with the push rod 112. The cam lever 118 has a cam lobe or edge 120 protruding into the slot 111 so that it will engage in the push rod 112 when the cam lever is moved to the desired position. The cam lever 118 urges the push rod 112 against a surface forming the slot and will retain the push rod from sliding longitudinally and changing the orientation of the heart valve holder at some undesired time. The cam is outside the patient, so it can be easily manipulated by a surgeon. The cam lock can be released so that the push rod 112 can be slid back and forth as desired.

A pulling force actuating device is shown in FIGS. 22, 23, 24 and 25, and in this form a handle and heart valve holder assembly 124 includes a heart valve holder 125 that is provided with a recess 126 in the center portion thereof. A pair of ears 127 are spaced apart to receive a slider link 128 that forms a connector to a handle 130. The edge of the heart valve holder 125 has an inclined surface 132, which is aligned with and abuts against an inclined surface 134 on the distal end of the handle 130. When the slider link 128 is retracted in a direction toward the proximal end of the handle 130, the slider link will pull the valve holder 125 so the surfaces 132 and 134 abut, and the moment created will cause the heart valve holder 125 to rotate about the axis of a pivot pin 129 which joins the ears 127 and the end of the slider link 128.

In this form of the invention, a screw 136 is threaded into the handle 130 adjacent the proximal end and is positioned to align with the slider 128 perpendicular to its axis so that once the slider is in a desired position the thumbscrew 136 can be tightened to hold the slider 128 securely relative to the handle 130. The holder thus can be locked in position.

Figure 26:
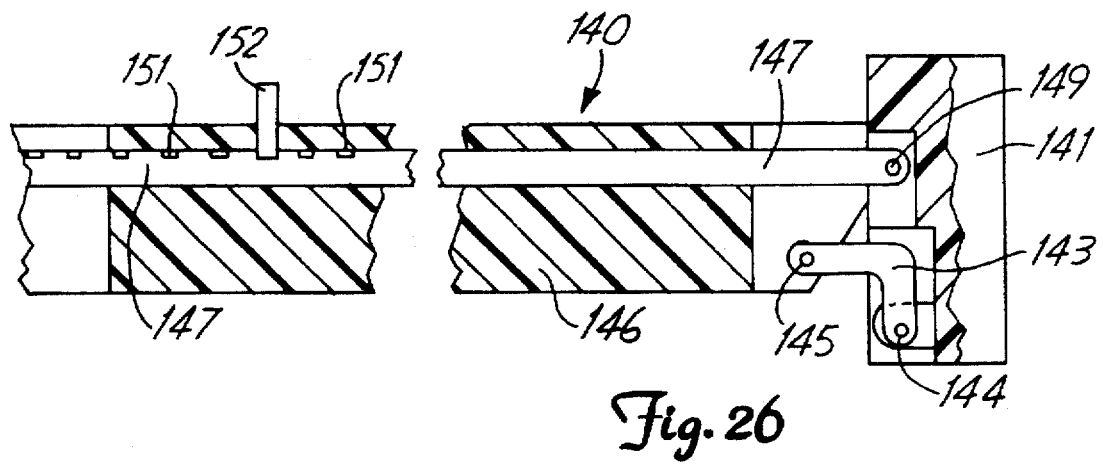
FIG. 26 is a further modified form of a pivoting mechanism utilizing a slider connection linkage made according to the present invention and including a lock pin engageable with a link for selectively locking slider movement.
Figure 27:
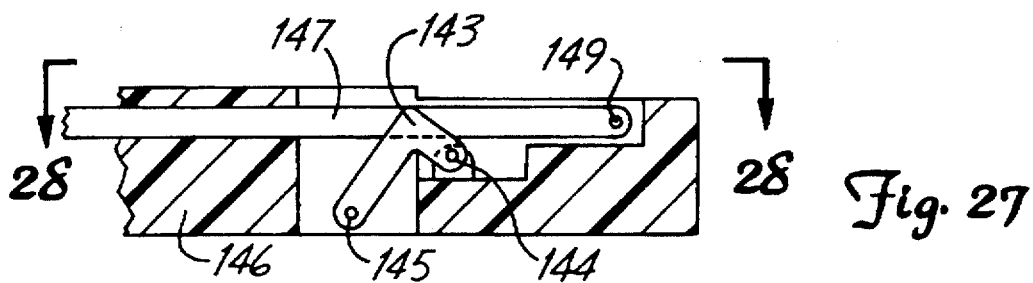
FIG. 27 is a side elevational view of the device in FIG. 26 with parts in section and with the heart valve holder in a modified position.
Figure 28:
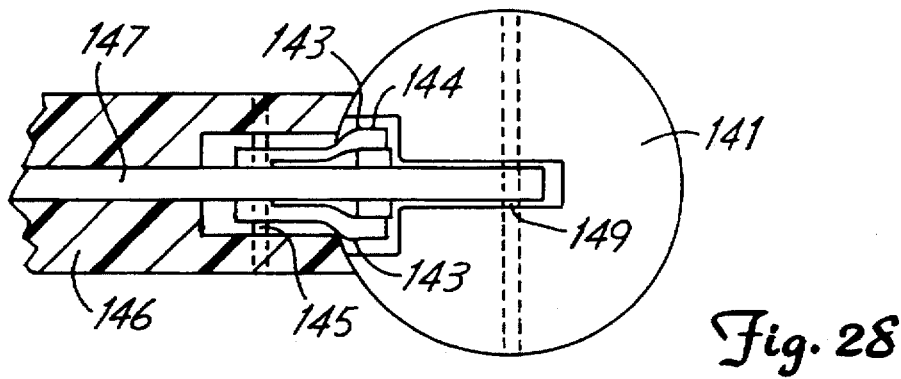
FIG. 28 is a plan view of the device of FIG. 27 taken on line 28—28 in FIG. 27.

In FIGS. 26, 27 and 28, a further slider arrangement is illustrated for pivoting a heart valve holder 141 relative to a handle 146 of a valve holder assembly 140. The heart valve holder 141 is provided with suitable connectors such as in a recess 142 for receiving a bellcrank link 143 that is pivotally mounted as at 144 at one end of the link to the heart valve holder, and is pivotally mounted at 145 adjacent to a distal end of handle 146.

A slider link 147 is slidably mounted in a suitable groove or bore in the handle 146. The slider link 147 forms a connector that is pivotally mounted as at 149 to the valve holder 141 at a position spaced from the pivot 144. With the heart valve holder in its position shown in FIG. 26, the slider link can be pushed out away from the handle 146, and the bellcrank 143 and slider link will pivot to cause the bellcrank 143 to in turn pivot and control movement of one edge of the valve holder 141 until the valve holder moves to its position shown in FIG. 27. The attachment of the links can be made with any desired type of pin or pivot connection. As shown in FIG. 28 the bellcrank link 143 may be bifurcated so the ends connected to the heart valve holder are spaced to accommodate link 147 when the heart valve holder is in position as shown in FIG. 27.

In this form of the invention, the slider link 147 is provided with a series of notches 151 on one edge thereof, and suitable apertures can be provided in the handle 146 through which a shear pin 152 maybe inserted to fit into one of the notches 151 and hold the slider link at a desired position. The slider link 147 can extend out beyond the proximal end of the handle 146 opposite from the valve holder 141.

Figure 29:
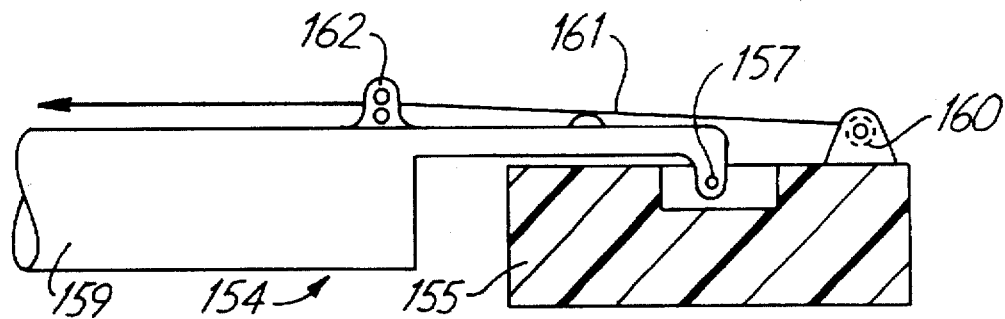
FIG. 29 is a part sectional schematic view of a cable actuator for pivoting a heart valve holder relative to a handle and made according to the present invention.
Figure 30:
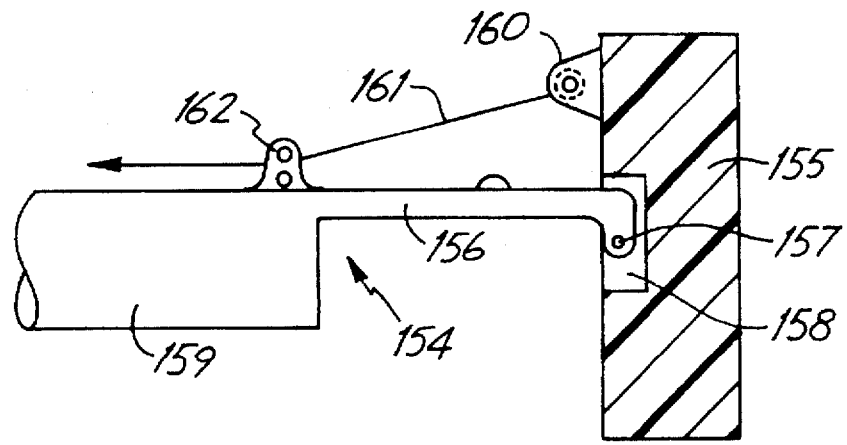
FIG. 30 is a side elevational view of the device of FIG. 29 in a second position.

FIGS. 29 and 30 illustrate a further modified form of the invention with a low profile handle and heart valve holder assembly 154 which includes a heart valve holder 155 and a connector link 156 pivotally mounted to the heart valve holder at 157, as previously explained using a suitable pivot pin. A recess 158 is formed in the heart valve holder for receiving an end portion of the connector link 156 to provide clearance for pivoting. The handle 159 is connected to the connector 156 and extends for a desired length.

In this form of the invention, the heart valve holder 155 has a tab 160 that extends upwardly from a proximal surface, and a cable 161 of small diameter is connected to the tab 160 and is passed through a guide 162. Guide 162 can be a pin passing between two protrusions through which the cable extends. The cable 161, as shown, can be pulled in a direction as indicated by the arrow, thus causing the heart valve holder 155 to pivot between the position shown in FIG. 29 and the position shown in FIG. 30.

The heart valve holder 155 can be returned to another position by external manipulation or by surgeons working within a chest cavity. The assembly 154 fits within any opening that would accommodate the heart valve holder 155 and a supported heart valve prosthesis in the position shown in FIG. 29. Pivot point 157 may also be affixed with a return spring mechanism which maintains constant tension on cable 161. When tension on cable 161 is released holder 155 will automatically return to the position shown in FIG. 29.

Figure 31:
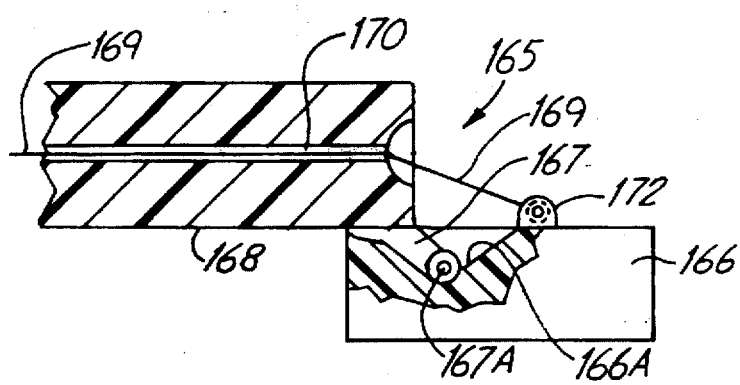
FIG. 31 is a part sectional view of a further modified pivoting mechanism for a heart valve holder utilizing a pull cable according to the present invention.
Figure 32:
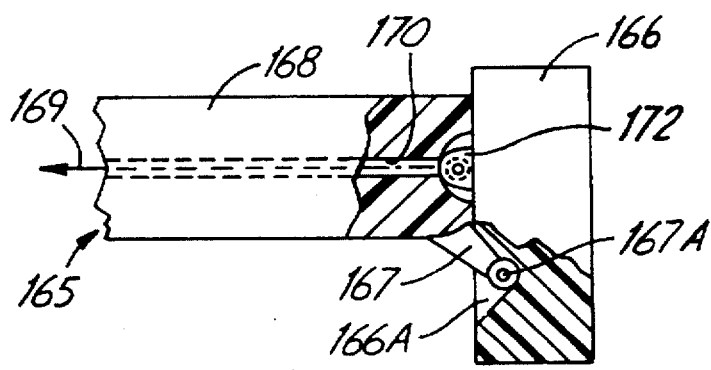
FIG. 32 is a side elevational view of the device of FIG. 31 with the heart valve holder in a second position.

The concept of using a pull cable for manipulating a heart valve holder is also illustrated in FIGS. 31 and 32. In this form of the invention, a heart valve holder and handle assembly 165 includes a heart valve holder 166 that has a connector 172 that receives a portion of one end of a handle 168.

A pull cable 169 is passed through a passageway 170 in the handle 168, and has one end connected to a suitable connector 172 on the proximal surface of the heart valve holder 166. A recess 166A is provided in holder 166 to receive distal protrusion 167 of handle 168. Distal protrusion 167 provides a location to house a suitable pivot pin 167A as previously discussed for other embodiments.

In this form of the invention the heart valve holder 166 can be held firmly in its position shown in FIG. 32, using a suitable locking mechanism on cable 169 as previously mentioned which is the position used for implanting. The holder 166 must be provided with an external force or a spring force applied to pivot point 167A for moving from the FIG. 32 position to the position shown at FIG. 31, when the cable is made slack.

The heart valve holder 166 can be manipulated to a desired position, and held tightly in its position shown in FIG. 32 for implantation.

Figure 33:
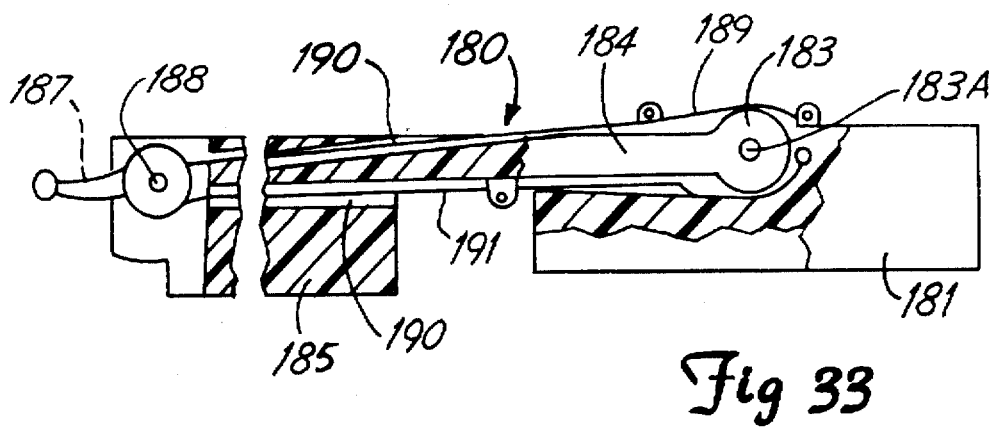
FIG. 33 is a side elevational view of a remotely actuated cable pivoting mechanism used with the heart valve holders of the present invention.
Figure 34:
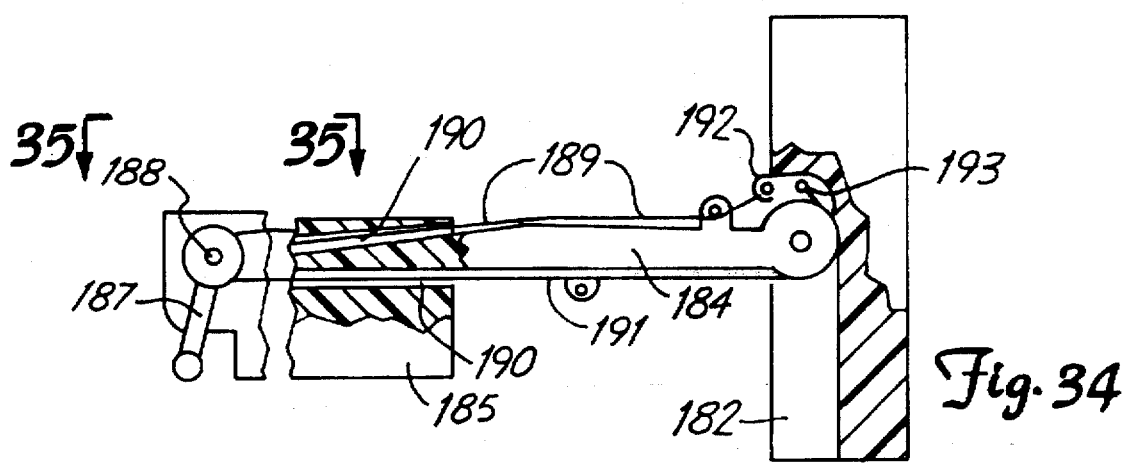
FIG. 34 is a view similar to that shown in FIG. 33 with the heart valve holder in a second position substantially 90° from the position shown in FIG. 33.
Figure 35:
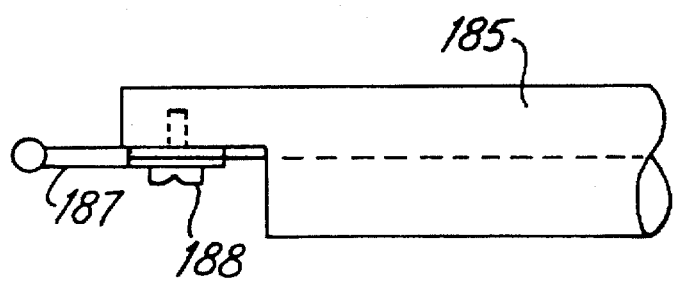
FIG. 35 is a fragmentary view of a handle portion taken on line 35—35 in FIG. 33.

FIGS. 33, 34 and 35 illustrate a heart valve holder and handle assembly 180 that includes a heart valve holder 181 that has a recess 182 for receiving the end portion of a connector 184 attached to a handle 185. The end portion 183 of the connector 184 is rounded for guiding cables, and is pivotally mounted with a pin 183A to the heart valve holder 181.

The handle 185 has an actuator lever 187 at the proximal end thereof. The lever 187 is pivotally mounted in a suitable manner and movable about a central pivot 188 formed by a threaded screw. The actuator lever 187 has two cables 189 and 191 connected to it. The cables 189, 191 in turn are connected at suitable locations 192 and 193 on the heart valve holder 181 respectively. The cable 189 is attached to a tab fixed to the heart valve holder. Cable 191 is attached with a suitable pin or small screw to hold the cable in position. The cables also pass through provided passageways 190, and guideways are provided as necessary for properly guiding the cables. The rounded end portion 183 guides the cables as well, as was stated.

When the lever 187 is in its position shown at FIG. 33, a heart valve holder 181 is in the position so that the plane of a heart valve prosthesis supported thereon would be parallel to the axis of the handle 185, and when the lever 181 is moved to position as shown in FIG. 34, cable 189 will be under tension and pull the heart valve holder 181 to its position shown in FIG. 34. Opposite movement of the lever 187 will cause opposite movement of the heart valve holder. The lever can be friction loaded with the threaded screw at pivot 188 to retain the lever in a desired position. The screw can be tightened to force the lever against the adjacent surface of the handle, preventing movement from the desired position.

FIGS. 36, 37 and 38 illustrate a worm gear driven actuator for pivoting the valve holder between two positions 90° apart, including the low profile position, and a position 90° to the low profile position.

A valve holder and handle assembly indicated generally at 210 includes a heart valve holder 211, that is formed with a recess 212, perhaps as best seen in FIG. 36. The recess 212 has a sector gear 213 therein that is fixed to the valve holder 211 in the center of the recess with suitable screws or the like 217. A gear 213 is positioned in a pocket or recess 214 shown in FIG. 36A formed in an end of a connector member 216 that is a part of a handle 218. The end of the connector 216 is pivotally mounted with pins 219 on each side of the bifurcated ends of connector 216 to the heart valve holder.

The gear 213 has gear teeth on it that mate with a worm gear 221 formed on the end of a rotating shaft 222 that is rotatably mounted in a bore in the handle 218. The shaft 222 is restrained from axial movement relative to the handle with a retainer ring or the like held in with a cap 220. When the shaft 222 is rotated, it will drive the worm gear 221 and in turn drive and pivot the gear 213.

This action will pivot the valve holder 211 between its position shown in FIG. 36 to its position in FIG. 37 under the gear drive between the worm 221 and the gear 213. Opposite rotation of the shaft moves the valve holder in an opposite direction. A worm gear set is self locking, so the valve holder is positively held in any position of pivoting.

Figure 39:
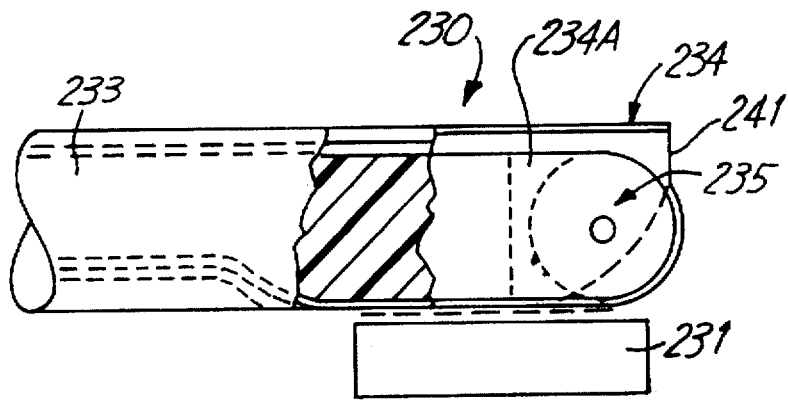
FIG. 39 is a side elevational view of a further modified form of the invention utilizing an endless belt or tape type mechanism for pivoting a valve holder about a pivot connection to a handle.
Figure 40:
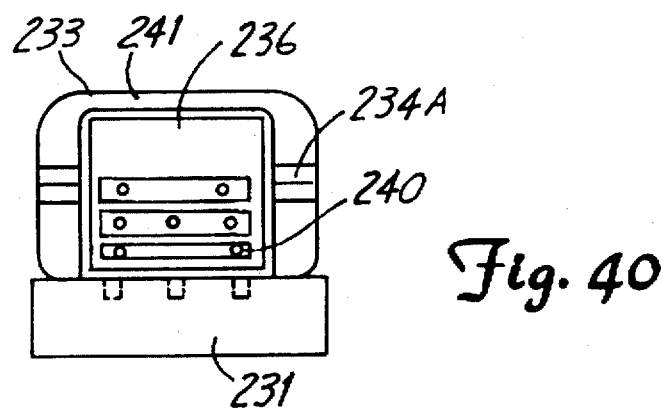
FIG. 40 is an end elevational view of the device of FIG. 39.
Figure 41:
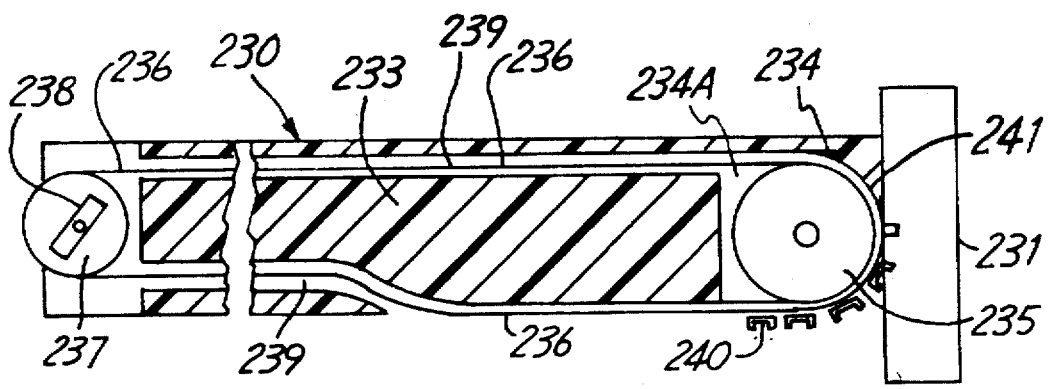
FIG. 41 is a side elevational view of the device of FIG. 39 with the valve holder in a second position.

FIGS. 39, 40 and 41 illustrate a way of utilizing an endless belt or chain for pivoting the valve holder relative to a handle. A valve holder and handle assembly shown at 230 in FIG. 39 has a valve holder 231 coupled to a handle 233. Handle 233 in turn includes a housing end 234 that has side members 234A (FIG. 40) which receive a narrow belt support roller 235, that is rotatably mounted on a shaft or end hinge supported in the side member 234A. The roller mounts a narrow belt 236 which is extended over a second roller 237 at a proximal end of the handle. The roller 236 is also suitably rotatably mounted and has a manual handle on lever 238 to permit rotating roller 237 and driving the belt 236 in either direction.

The belt 236 is guided through passageways 239 formed in the handle 233. The belt 236 carries a selected number of cleats 240, which may be part of a roller chain fastened to an outer surface of the belt 236. The heart valve holder 231 is secured to one of the cleats 240 with suitable fasteners so that the heart valve holder 231 moves with the belt 236. The heart valve holder 231 thus can be moved between the positions shown in FIGS. 39 and 41. The belt movement is positive. The end surface 241 of the handle 233 forms a positive stop for the holder.

Figure 42:
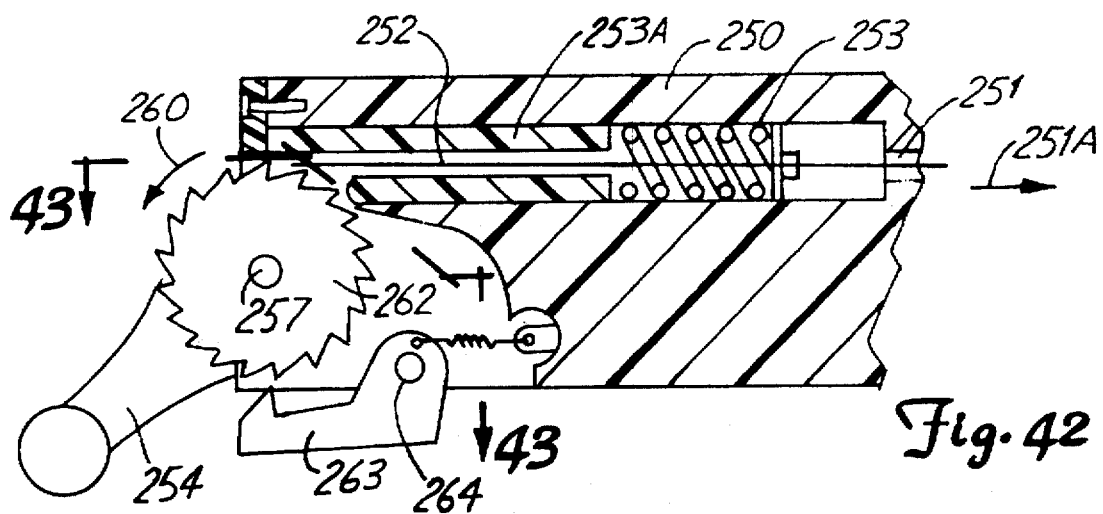
FIG. 42 is a schematic side elevational representation of a cable actuator used with one of the previous forms of the invention illustrating a spring return for cable, with a rachet lock on the control lever to maintain the cable in its desired position.
Figure 43:
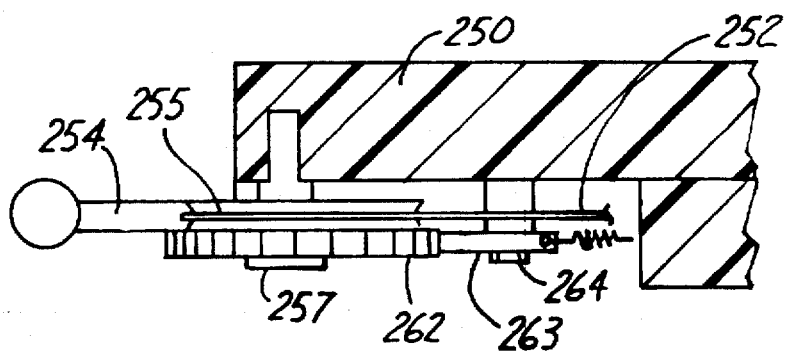
FIG. 43 is a sectional view of the actuating lever with a ratchet lock mechanism shown in FIG. 42 and taken on line 43—43 in FIG. 42.

FIG. 42 is a schematic illustration of a spring return when a cable and operating lever are used for manipulating a heart valve holder according to the present invention. The handle member 250 is provided with an internal passageway 251 for carrying an actuator cable 252. The passageway 251 has an end section 251A that is large enough to carry a coil spring 253 which is captured in the passageway 251 with a tubular sleeve 253A secured in the end section 251A after the spring is in place. The cable 252 passes through the opening in sleeve 253A. The outer end of spring 253 is secured to the cable 251 and the inner end abuts against the end of the sleeve 253A.

The spring 253 as shown is a compression type spring. The cable extends over a pulley like hub 255 secured to lever 254. The cable is secured to the hub 255. When the cable 251 is actuated with the pivoting lever 254, moving counter clockwise, the cable 251 will be spring loaded in a direction as indicated by the arrow 251A, tending to return to the cable's initial position. The lever 254 is mounted on a pivot 257.

A pawl and ratchet type arrangement prevents clockwise movement of the lever 254 unless the pawl is released. As shown, ratchet wheel 262 is fixed to move with the lever, and a spring loaded ratchet pawl 263 rides against the teeth of the ratchet 262.

The ratchet is oriented such that the lever 254 can be moved in counter clockwise direction as indicated by the arrow 260, but the ratchet pawl will latch into a respective tooth of the ratchet wheel 262 to hold the lever 254 in a desired position against the loading of the spring 253.

The pawl can be manually released against its spring load that tends to hold the ratchet pawl against the ratchet teeth as the pawl moves about a pivot 264, so that the lever 254 can pivot, and cable 252 will then be urged as indicated by the arrow 251A in FIG. 42.

Figure 44:
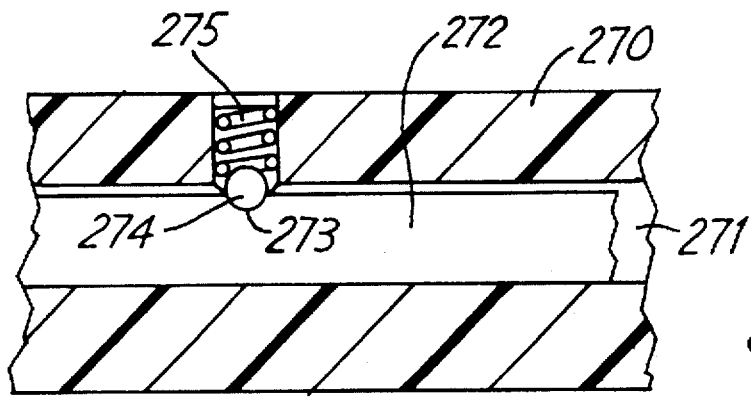
FIG. 44 is a fragmentary sectional view of a typical handle made according to the present invention showing a push rod or slider actuator held in a desired location by use of a spring loaded detent.

In FIG. 44 a schematic representation of a typical detent arrangement for retaining a push rod or slider relative to a handle is illustrated. In this form of the invention, a handle 270 has a bore 271 that receives a slider 272, which can be one of the actuating sliders shown in previous forms of the invention. The slider 272 has a recess 273 on one edge thereof. This recess is positioned along the axis of the slider 272 at a location so that when the slider 272 is in a desired position a detent ball 274 will enter the recess 273 and hold the slider preventing longitudinal movement. The ball 274 is made in a conventional manner and is spring loaded with a spring 275. The ball 274 is made so that it will not pass through the bore that is provided for the ball 274 in a normal manner.

Figure 45:
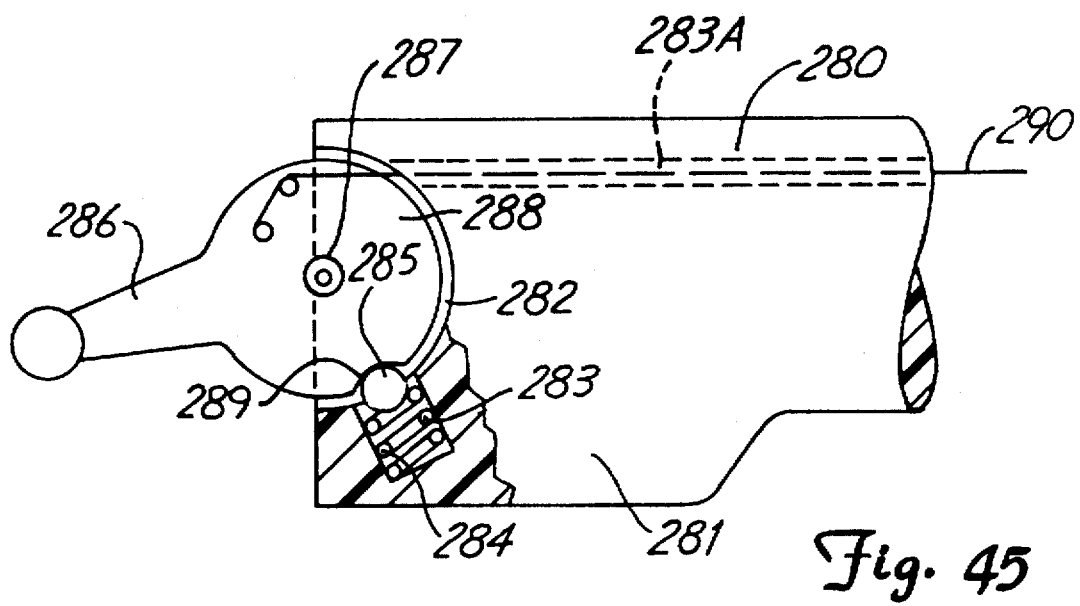
FIG. 45 is a schematic representation of the end of a handle and lever used with the present invention using a cable actuating lever and illustrating the use of a spring loaded ball detent for retaining an actuator in a desired position for holding the valve holder at its proper orientation.
Figure 46:
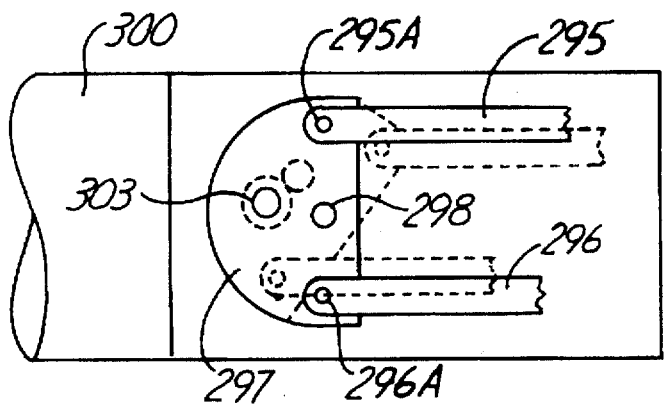
FIG. 46 is a schematic side elevational view of an actuator lever for a 4-bar linkage and having a spring loaded detent in position to retain the actuator links in a desired position.

The detent ball operating on a control lever such as that shown in FIG. 42 also can be utilized as shown in FIG. 45. In this form of the invention, a handle 280 has a lever mounting block 281 formed thereon. The block 281 is provided with a recess or offset 282 that has a flat mounting surface. The handle has a bore 283 that houses a spring 284 and a detent ball 285. The lever 286 is pivotally mounted on a pin 287 to the handle, with the actuating end of the lever extending out beyond the proximal end of the handle 280. The lever has a disc 288 that has a recess 289 for receiving the ball 285 when the recess 289 aligns with the ball 285. In this position, a cable 290 that is utilized with the lever 286 is secured to the disc (which acts as a pulley) retained in the detented position until the force of the detent ball 285 is overcome from force on the lever which causes the ball 285 to retract and be released from the receptacle 289.

The cable passes through a bore 283A in the handle 280 and is connected to a heart valve holder for controlling the heart valve holder position.

Figure 47:
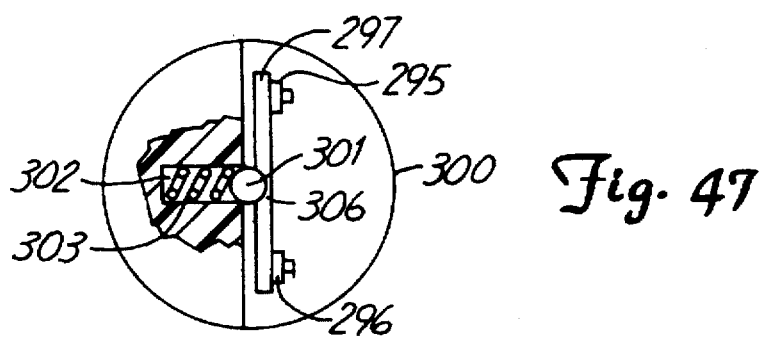
FIG. 47 is an end view of the device of FIG. 46 with parts broken away.
Figure 48:
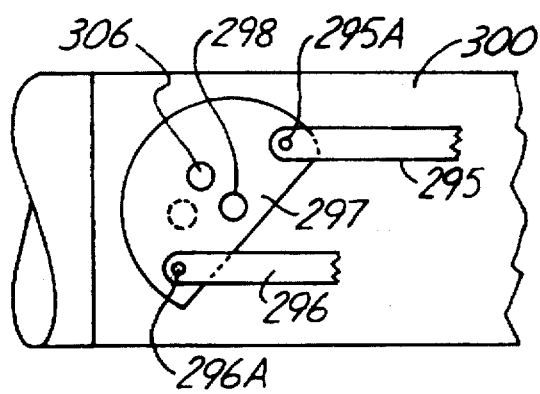
FIG. 48 is a side view of the device of FIG. 46 with the actuating lever in a released position.
Figure 49:
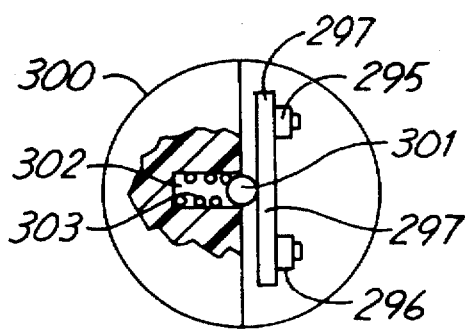
FIG. 49 is an end elevational view of the device of FIG. 48 with parts in section.

Illustratively shown in FIGS. 46–49 is also a detent ball retainer that can be used with linkages. For example, links 295 and 296, would be connected to a heart valve holder, and pivotally mounted as at 295A and 296A on a control link or disc 297. The disc or link is mounted on a pivot pin 298 in a suitable location on the side of a handle 300. A detent ball 301 is mounted in a recess 302 in the handle 300 at a desired location. A suitable spring 303 loads the ball 301 so the ball will be partly protruding out of the surface on which the control disc or link 297 is mounted. In a detent or working position as shown in FIG. 47 the ball 301 will be engaging a hole which forms a receptacle 306 in the disc 297. However, when the control link 297 is moved to its position shown in FIGS. 48 and 49, the ball moves out of the receptacle 306 that receives the ball 301 to permit movement. The detent force on the control disc or link 297 will hold the disc in a desired position to hold a heart valve holder that is coupled to the links 295 and 296 in a desired position.

Figure 50:
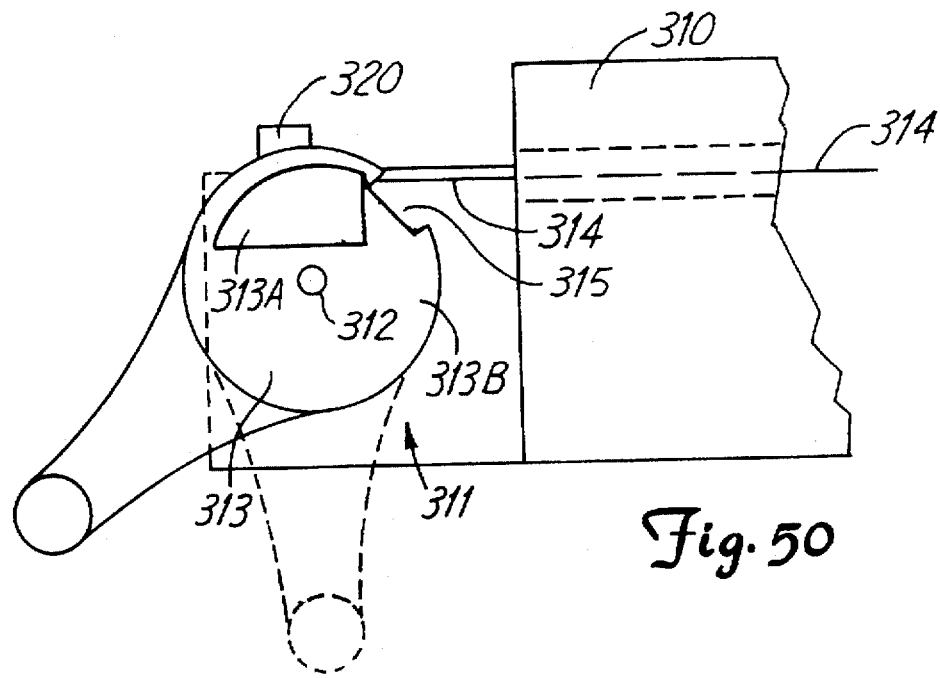
FIG. 50 is a schematic representation of a lever having a latch type dog that fits into a receptacle on the lever for maintaining a cable in a desired position.
Figure 51:
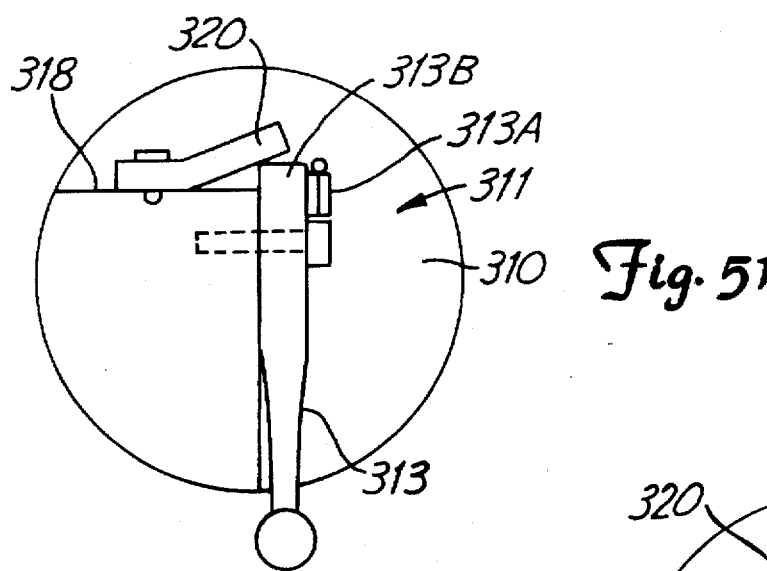
FIG. 51 is an end elevational view of the device of FIG. 50 showing the latch dog in released position.
Figure 52:
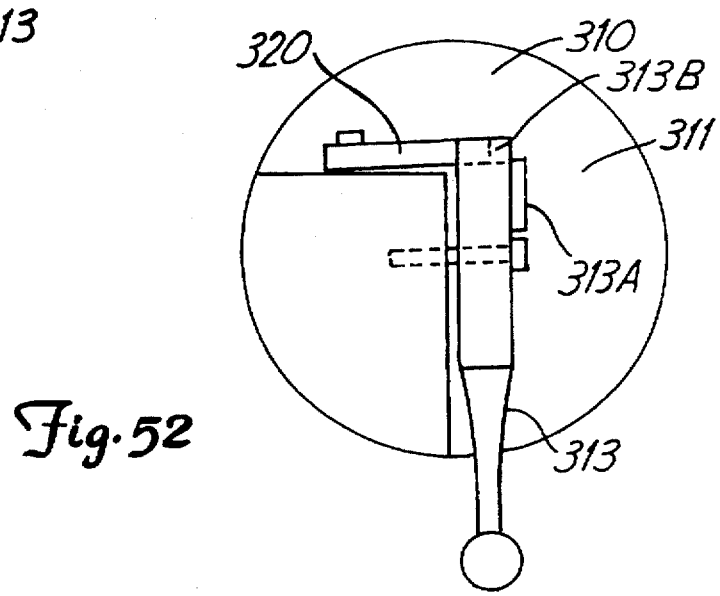
FIG. 52 is an end elevational view of the device of FIG. 50 showing the latch dog in an engaged position in the receptacle on the lever.

FIGS. 50, 51, and 52 show an alternate embodiment of the present invention utilizing a spring latch detent for holding a lever in a desired position when actuating a heart valve holder.

In FIG. 50, a handle 310 is provided with mounting portion 311 at its proximal end, that in turn mounts a pivot pin 312 for pivotally mounting a control lever 313. Control lever 313 has a pulley sector 313A offset from the main disc 313B of the lever, which mounts and actuates a cable 314, as previously disclosed.

The disc 313B has a notch 315 in an outer periphery of disc portion 313B of the lever 313. The end of the handle 310 can be configured as shown in FIG. 50 and a ledge 318 is provided along side the recess 311. The ledge 318 mounts one end of a leaf spring 320. The spring 320 is cantilevered and extends over and rides onto the edge of the disc 313B. When the lever 313 is in the position shown in FIG. 50, the spring merely rides on the outer periphery of the disc 313B, but when the lever is moved to the position shown in dotted lines in FIG. 50 and in FIG. 52, the notch 315 aligns with the cantilevered end of spring 320 and the spring 320 latches in place in the notch 315 so that it will secure the lever 313 against movement, and will resist any loads on the cable 314. If the cable 314 is under tension at this stage, from moving the heart valve holder coupled to this cable to a desired position, the heart valve holder will also be maintained in the proper position for manipulation.

Figure 53:
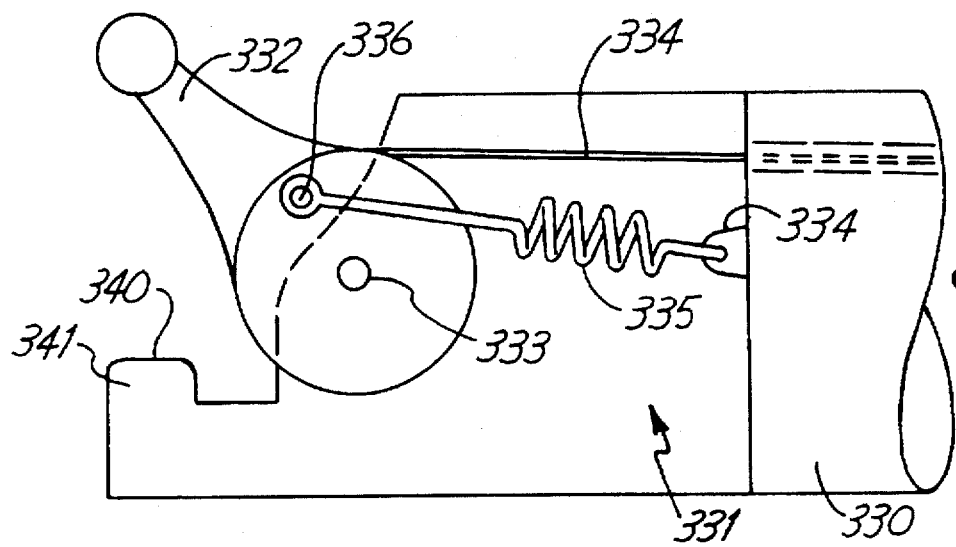
FIG. 53 is a schematic side elevational view of a lever in a first position for a toggle lock arrangement.
Figure 54:
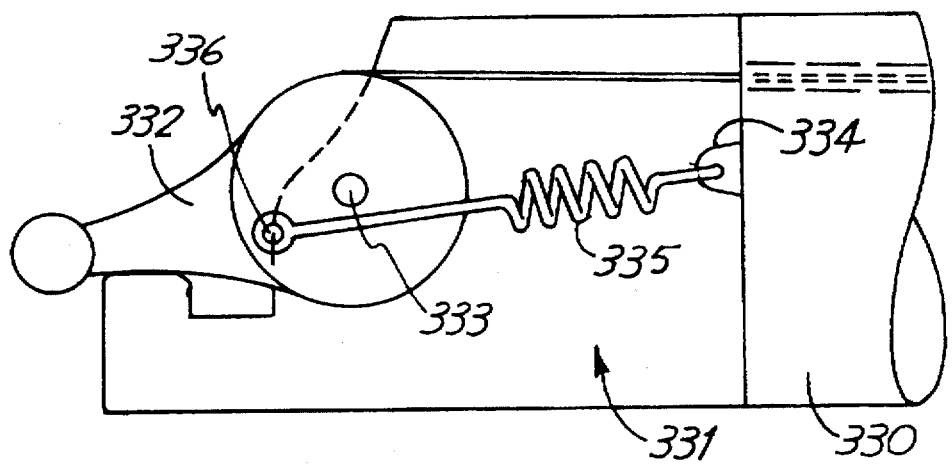
FIG. 54 is a view of the toggle lock of FIG. 53 in a locked position.
Figure 55:
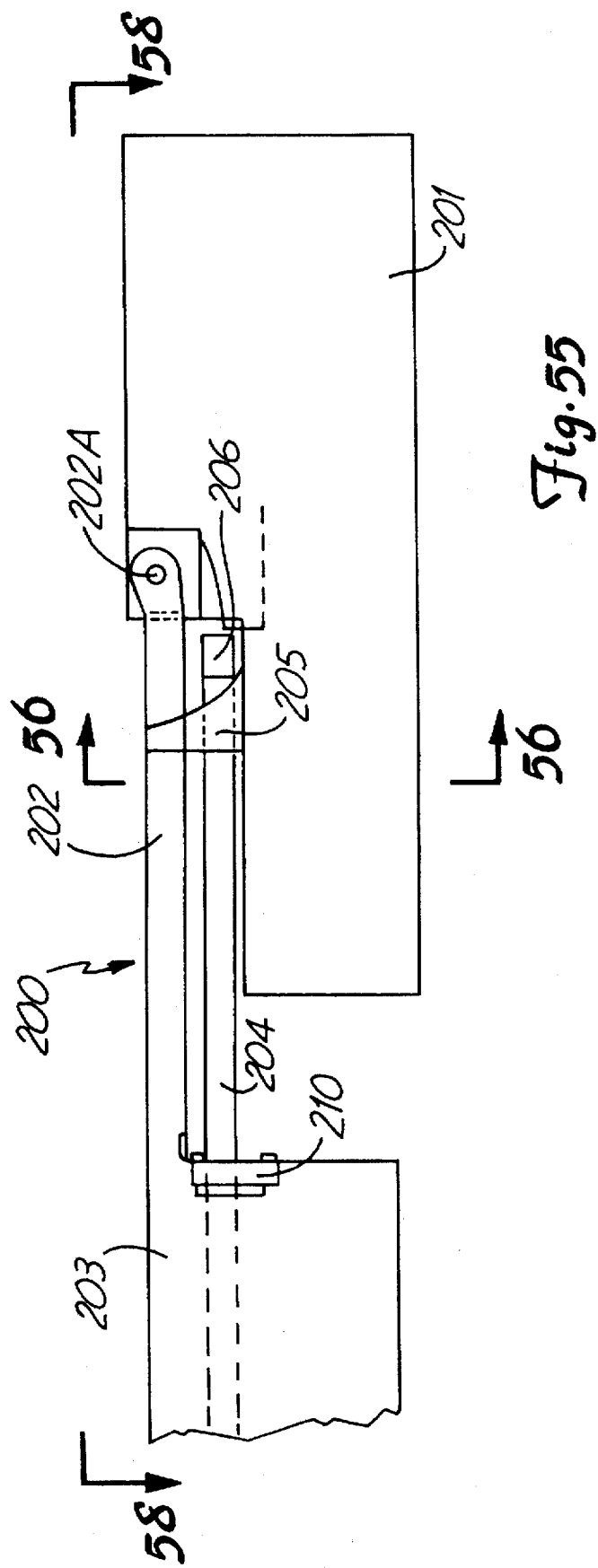
FIG. 55 is an enlarged side view of a further modified form of the actuator for pivoting the heart valve holder in accordance with the present invention using a cam actuator.
Figure 56:
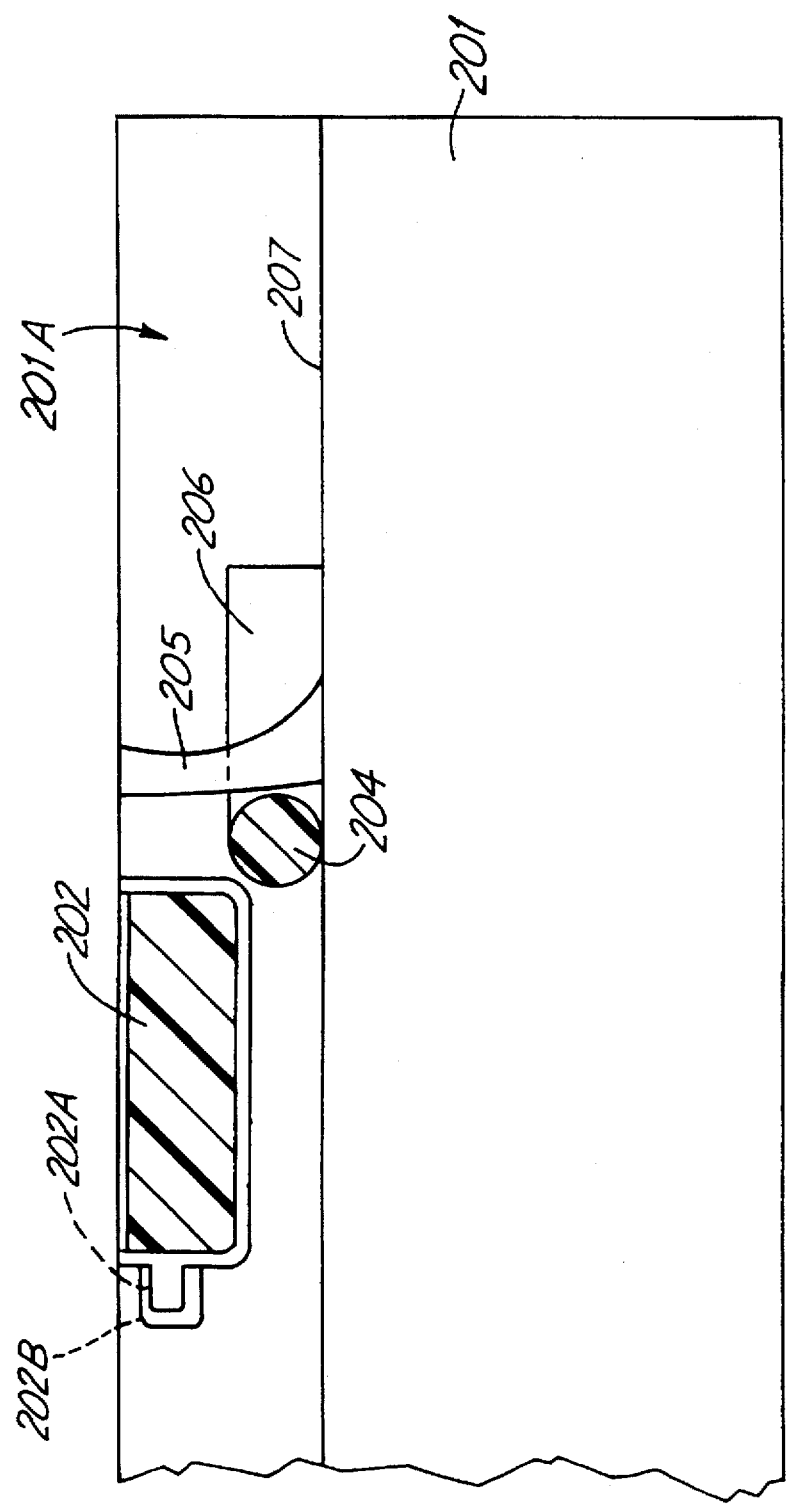
FIG. 56 is an enlarged sectional view taken as on line 56—56 in FIG. 55.

A locking mechanism utilizing an over center lock is shown in FIGS. 53 and 54. In this form of the invention, a heart valve holder handle 330 is provided with a recess 331 at its proximal end for pivotally mounting a lever 332 on a pivot pin 333. The lever has a control cable 334 connected thereto as previously explained, and the control cable would be attached to a heart valve holder as shown in one of the forms of the invention previously illustrated. In this instance, the end wall of the recess 331 supports a mounting ear 334 for mounting one end of a tension spring 335. The opposite end of the tension spring is mounted on a pin 336 to the disc portion of the lever 332. In the position shown in FIG. 53 the cable 334 would be slack, or under light load, and upon moving the lever to its position as shown in FIG. 54, the cable is loaded, for example, by the heart valve holder engaging a stop, or by a spring load and previously shown. The spring 335 goes "over center" relative to the pivot pin 333, and the spring force tends to hold the lever 332 down against a stop surface 340 provided on a protruding part of the handle in a suitable manner. As shown, stop surface 332 is an upper surface of a lug 341 that projects from the handle 330.

Actuation of the heart valve holders from a first position to a second position can be accomplished by other mechanisms. A cam actuator is schematically shown in FIGS. 55, 56, 57 and 58. The handle and valve holder assembly 200 includes a valve holder 201 that is pivotally connected through a connector link 202 to a handle 203. The distal end of the connector link has extending pivot pins 202A that are pivotally mounted in sockets 202B formed in the heart valve holder 201.

A rotatable cam shaft 204 is rotatably mounted in a suitable bore in the handle 203. The cam shaft has a cam lobe 205 overlying the surface 207 of a recessed section 201A of the heart valve holder 201.

The cam shaft is held from axial movement in the bore of the handle in a suitable manner, such as a thrust washer held with a suitable cap 210.

Figure 57:
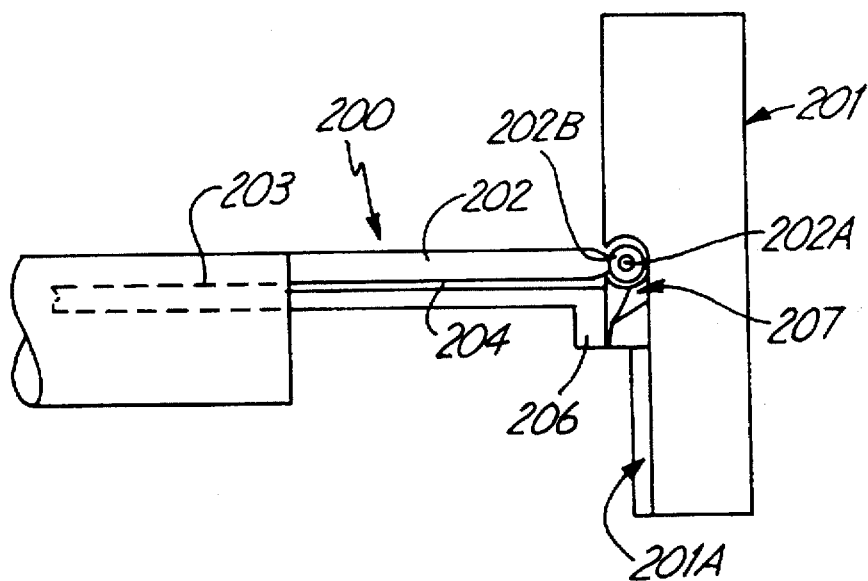
FIG. 57 is a side elevational view of the device of FIG. 55 shown with the heart valve holder pivoted 90° from the position in FIG. 55.
Figure 58:
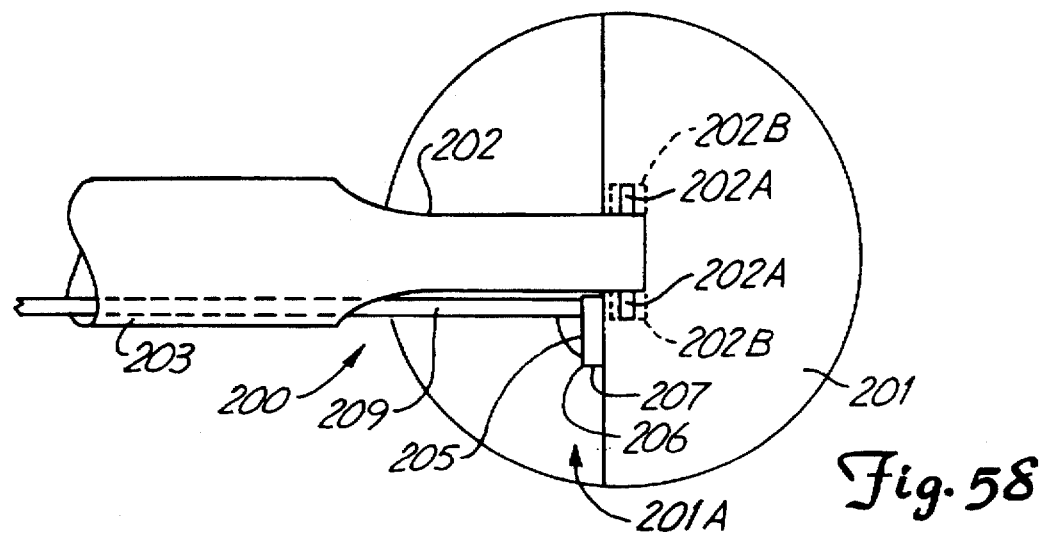
FIG. 58 is a top plan view taken as on line 58—58 in FIG. 55.

The rod 204 carries a cam member or lobe 206 that is, as shown, in a first position resting on the surface 207 formed by the recess 201A of the heart valve holder 201. In this position, the valve holder 201 can be moved to its second position as shown in FIG. 57. By rotating the cam shaft 202, the cam lobe will act on the surface 207 to start to pivot the heart valve holder about the pivot pins 202A to a position shown in FIG. 57. In order to reach a full 90° of pivoting, a cam track 205 is formed above surface 207 to be engaged by the cam. After the cam shaft has been rotated a certain amount, the cam shaft and cam track are offset from the centerline of the handle so the connector 202 has clearance when the heart valve holder 201 is in the position shown in FIG. 58. The cam track can be formed to accommodate movement of the cam.

The cam can be used for rotating the heart valve holder at least 90° the cam riding on the ramp will support the heart valve holder and prevent it from moving back to its original position.

In all of the forms of the invention shown, various actuating devices for pivoting heart valve holders between at least two positions 90° from each other are illustrated. In the descriptions, the pivoting takes place from a position wherein a plane of the heart valve ring is parallel to the axis of the handle, and to a second position wherein the plane of the heart valve ring would be perpendicular to the axis of the handle. Stated another way, and meaning the same thing, is to have the axis of the orifice, that is the central axis of the ring of the heart valve prosthesis itself, perpendicular to the axis of the handle in one position and parallel to the axis of the handle in the other position.

Further, it is desirable to maintain the handle, and its mounting mechanisms on the heart valve holder within the periphery of a heart valve orifice and suture cuff that would be mounted on the heart valve holder shown.

These devices comprising pivoting linkages, sliders, pull cables, gear mechanisms, cams and the like solve the problem of manipulating a heart valve prosthesis mounted on the heart valve holder. The hinges can be integral with the heart valve holders, or separate hinging mechanisms can be utilized. The hinging mechanisms and actuators provide a method of moving the heart valve holder, and a heart valve mounted on the holder from a position with the axis of the handle parallel with the axis of the orifice of the heart valve orifice to a position where the handle axis is perpendicular to the axis of the orifice of the heart valve.

The heart valve holders have to be capable of being actuated from a remote point, where the surgeon cannot manually contact the valve and valve holder assembly. In other words, the surgeon must be able to actuate the mechanism from a point on the handle remote from the heart valve holder and a heart valve mounted on the holder. This requirement is particularly important in the use of a trocar or similar device for insertion of the valve and the suturing the valve into place for implanting. The material used can be any material compatible with the implantation of heart valves, including polymers.

Although the present invention has been described with reference to preferred embodiments, workers skilled in the art will recognize that changes may be made in form and detail without departing from the spirit and scope of the invention.

What is claimed is:

1. A low profile heart valve holder assembly comprising:
   a valve holder body sized for fitting within and supporting a heart valve orifice ring, said heart valve holder defining a plane and having a generally disk-like shape within said plane;
   a handle; and
   a pivot connection between the handle and the valve holder body permitting pivoting movement of substantially 90° of the valve holder body between first and second positions while supporting a heart valve orifice ring.

2. The low profile heart valve holder assembly of claim 1, wherein the pivot connection is within a space bounded by the valve holder body.

3. The low profile heart valve holder assembly of claim 1, wherein said valve holder body has an upper surface, the pivot connection being coupled to the upper surface and providing pivoting movement of the handle between a position where the handle is substantially on a plane with the upper surface of the valve holder body to a position wherein the valve holder body has been rotated substantially 90° relative to the handle.

4. The low profile heart valve holder assembly of claim 1, including and an actuator coupled to the valve holder body and extending to a remote location on the handle for remotely actuating the pivoting of the valve holder body.

5. The low profile heart valve holder assembly of claim 4, wherein said actuator comprises a link pivotally mounted to the valve holder at a position spaced from the pivot connection between the handle and the valve holder and extending along the handle.

6. The low profile heart valve holder assembly of claim 4, wherein said actuator comprises a flexible cable connected to the valve holder at a position spaced from the pivot connection coupling the handle to the valve holder, and extends along a handle coupled to the handle connector.

7. The low profile heart valve holder assembly of claim 4, wherein said actuator comprises a four-bar linkage having two links pivotally mounted to the valve holder at spaced locations thereon, said two links being pivotally mounted on separate pivots to form a parallelogram, said separate pivots to form a parallelogram being coupled to said handle.

8. The low profile heart valve holder assembly of claim 7, wherein said pivotal mounting of said links coupled to said handle comprises a third link pivotally mounted with respect to the handle and having the separate pivots thereon, whereby pivoting of said third link on its pivotal mounting to the handle causes said first and second links to change the orientation of the valve holder relative to the hinge mounting of the handle connector.

9. The low profile heart valve holder assembly of claim 4 and a pivoting lever mounted on the a handle at a location spaced from the valve holder for operation by a user of the valve holder, the pivoting lever being coupled to a cable to cause the cable to extend and retract to cause pivoting of the valve holder.

10. The low profile heart valve holder assembly of claim 4, wherein there is a stop member between the actuator and the handle to retain the actuator in a desired position relative to the handle.

11. The low profile heart valve holder of claim 10, wherein the actuator comprises an elongated sliding member moving relative to the handle, said stop member comprising a screw tightenable onto the elongated sliding member to provide a friction load on the sliding member.

12. The low profile heart valve holder assembly of claim 10, wherein said actuator comprises a link sliding in a bore in the handle, and wherein stop member comprises a pin insertable into a receptacle in the link to prevent sliding movement of the link.

13. A low profile heart valve holder and handle assembly comprising a heart valve holder adapted to retain a heart valve orifice ring thereon, said heart valve holder defining a plane and having a generally disk-like shape within said plane;

a handle for manipulating the heart valve holder and having a longitudinal axis;

a hinge connection for hingedly coupling the handle to the heart valve holder, said hinge connection permitting movement of the heart valve holder about an axis substantially parallel to the plane of the heart valve holder and perpendicular to the longitudinal axis, and permitting movement of the heart valve holder from a position with said plane of the heart valve holder substantially parallel to the longitudinal axis, to a second position with said plane of the heart valve holder substantially 90° to the longitudinal axis with a heart valve orifice ring supported on the heart valve holder;

the hinge connection being substantially within the periphery of the heart valve holder.

14. The heart valve holder and handle assembly of claim 13, wherein said hinge connection comprises a flexible section of material coupling the handle to the heart valve holder.

15. The low profile heart valve holder and handle assembly of claim 14, wherein said flexible material is integrally formed with the heart valve holder.

16. The low profile heart valve holder and handle assembly of claim 14, wherein the flexible material section is a separate strap of flexible material attached to the heart valve holder and attached to the handle.

17. The low profile heart valve holder and handle assembly of claim 13, wherein the hinge connection comprises a ball and socket connection between the heart valve holder and the handle.

18. The low profile heart valve holder and handle assembly of claim 13, wherein the hinge connection comprises a pivot pin extending between aligning portions of the heart valve holder and the handle.

19. The low profile heart valve holder and handle assembly of claim 13 further including an actuator supported on the handle and connected to the heart valve holder and operable for causing hinging movement of the heart valve holder on its hinge connection to the handle.

20. The heart valve holder and handle assembly of claim 19, wherein the actuator comprises a rotatable cam lobe rotatably mounted on the handle and engaging the heart valve holder such that when rotated the cam lobe causes pivoting of the heart valve holder.

21. The heart valve holder and handle assembly of claim 19, wherein the actuator comprises a worm and gear, the gear being fixed on the heart valve holder and the worm being rotatably mounted on the handle, a center of the gear being mounted to be substantially coincident with the axis of movement of the hinge connection.

22. The low profile heart valve holder of claim 13, wherein the handle includes a central slider hingedly mounted to the heart valve holder, and an outer member slidably mounted on the slider and longitudinally movable to engage the heart valve holder in its first position and to move the heart valve holder to its second position.

* * * * *